US012662535B2

(12) United States Patent
Tseng

(10) Patent No.: US 12,662,535 B2
(45) Date of Patent: Jun. 23, 2026

(54) PRO-ANTIBODY THAT REDUCES OFF-TARGET TOXICITY

(71) Applicant: IMMUNELOGIC THERAPEUTICS, INC., Beijing (CN)

(72) Inventor: Kuo-Fu Tseng, Dallas, TX (US)

(73) Assignee: IMMUNELOGIC THERAPEUTICS, INC., Beijing (CN)

( * ) Notice: Subject to any disclaimer, the term of this patent is extended or adjusted under 35 U.S.C. 154(b) by 558 days.

(21) Appl. No.: 17/150,626

(22) Filed: Jan. 15, 2021

(65) Prior Publication Data

US 2021/0301015 A1 Sep. 30, 2021

Related U.S. Application Data

(60) Provisional application No. 62/962,555, filed on Jan. 17, 2020.

(51) Int. Cl.
| | |
|---|---|
| *C07K 16/28* | (2006.01) |
| *A61K 35/17* | (2015.01) |
| *A61K 45/06* | (2006.01) |

(52) U.S. Cl.
CPC .......... *C07K 16/2809* (2013.01); *A61K 35/17* (2013.01); *A61K 45/06* (2013.01); *C07K 16/2878* (2013.01); *C07K 2317/56* (2013.01); *C07K 2319/03* (2013.01); *C07K 2319/30* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |
| 5,712,120 | A | 1/1998 | Rodriguez et al. |
| 5,861,155 | A | 1/1999 | Lin |
| 5,869,619 | A | 2/1999 | Studnicka |
| 6,054,927 | A | 4/2000 | Brickell |
| 6,180,370 | B1 | 1/2001 | Queen et al. |
| 8,541,203 | B2 | 9/2013 | Daugherty et al. |
| 10,059,762 | B2 | 8/2018 | Stagliano |
| 10,233,244 | B2 | 3/2019 | Sagert |
| 10,822,419 | B2 | 11/2020 | Wang et al. |
| 2016/0068601 | A1* | 3/2016 | Brogdon ............ A61K 40/4211 |
| | | | 536/23.53 |
| 2018/0271997 | A1 | 9/2018 | Wang |
| 2018/0333507 | A1 | 11/2018 | Lowman et al. |
| 2019/0076524 | A1* | 3/2019 | May ................. A61K 39/39558 |
| 2019/0359714 | A1 | 11/2019 | Tipton |
| 2021/0301019 | A1 | 9/2021 | Tseng |
| 2022/0324975 | A1 | 10/2022 | Sakurai et al. |

FOREIGN PATENT DOCUMENTS

| | | |
|---|---|---|
| CA | 2 865 482 | 9/2013 |
| CA | 3 042 679 | 5/2018 |
| CN | 107709356 | 2/2018 |
| CN | 113905757 | 1/2022 |
| CN | 115551892 | 12/2022 |
| EP | 3 808 376 | 4/2021 |
| EP | 4 023 230 | 7/2022 |
| JP | 2015-509952 | 4/2015 |
| JP | 2020-514935 | 5/2020 |
| WO | 2004092338 A2 | 10/2004 |
| WO | WO-2016210447 A1 * | 12/2016 .............. A61P 35/00 |
| WO | 2017156178 A1 | 9/2017 |
| WO | 2019051102 A2 | 3/2019 |
| WO | 2019/075405 | 4/2019 |
| WO | 2019/242505 | 12/2019 |
| WO | 2020/246563 | 12/2020 |
| WO | 2021/195472 | 9/2021 |

OTHER PUBLICATIONS

Liao et al (Anticancer Research, 21(3B)L1673-1680, 2001, abstract only).*
Lee et al (Moleuclar Immunology, 36:61-71, 1999).*
United States Patent & Trademark Office (ISA), International Search Report and Written Opinion for PCT/US21/13688 dated Sep. 23, 2021, 20 pp.
China National Intellectual Property Administration, Examination Report for China Patent Appl. No. 202180009547.6 dated Oct. 25, 2023 (with translation) 25 pp.
Australian Government, IP Australia, Examination Report for AU Appl. No. 2021208642 dated Jun. 21, 2024.
European Patent Office, Extended European Search for EP Appl. No. 21741991.0 Dated Feb. 27, 2024, 12 pp.
Lang, et al. "LegoBody: facile generation of bispecific and multi-specific antibodies" bioRxiv preprint doi: https://doi.org/10.1101 /2019.12.25.888586; this version posted Dec. 27, 2019.
Xin Zheng et al., "Effects of MMP14 Monoclonal Antibody on Proliferation and Apoptosis of Oral Squamous Cell Carcinoma", Biotechnology, vol. 33, No. 2, pp. 157-163 (2023), with English abstract.
First Office Action issued Oct. 25, 2023 in Chinese Patent Application No. 202180009547.6, with English translation.

(Continued)

*Primary Examiner* — Brad Duffy
(74) *Attorney, Agent, or Firm* — Wenderoth, Lind & Ponack, L.L.P.

(57) ABSTRACT

The present invention includes proteins, nucleic acids and methods of making and using an activatable antibody (aAb) comprising, in order, the following structure: a first light chain comprising: a first variable light region; a cleavable linker; a first heavy chain comprising: a first variable heavy region; wherein the cleavable linker prevents or reduces the first light chain and the first heavy chain from forming a first antigen binding site against a first antigen; and wherein cleavage of the cleavable linker releases the first heavy chain to allow formation of the first antigen binding site to bind a first antigen.

31 Claims, 8 Drawing Sheets

Specification includes a Sequence Listing.

(56) References Cited

OTHER PUBLICATIONS

Office Action issued Aug. 15, 2024 in Canadian Patent Application
No. 3,165,414.
Extended European Search Report issued Feb. 27, 2024 in European
Patent Application No. 21741991.0.

* cited by examiner

PRO-ANTIBODY THAT REDUCES OFF-TARGET TOXICITY

CROSS-REFERENCE TO RELATED APPLICATIONS

This application claims priority to U.S. Provisional Application Ser. No. 62/905,027, filed Sep. 24, 2019, the entire contents of which are incorporated herein by reference.

TECHNICAL FIELD OF THE INVENTION

The present invention relates in general to the field of pro-antibodies (probodies) that reduce normal tissue targeting and that enhance tumor targeting.

STATEMENT OF FEDERALLY FUNDED RESEARCH

Not applicable.

REFERENCE TO A SEQUENCE LISTING

The Sequence Listing in an TXT file, named as AEBI1000.txt of 19 KB, created on Aug. 30, 2023, and submitted to the United States Patent and Trademark Office via Patent Center, is incorporated herein by reference.

BACKGROUND OF THE INVENTION

Without limiting the scope of the invention, its background is described in connection with probodies, or activatable antibodies.

One such probody is taught in U.S. Pat. No. 10,059,762, issued to Stagliano, et al., entitled, "Anti-EGFR activatable antibodies". These inventors teach modified antibodies that contain an antibody or antibody fragment (AB) modified with a masking moiety (MM), which can be further coupled to a cleavable moiety (CM), resulting in activatable antibodies (AAs). In the AA, the CM is capable of being cleaved, reduced, photolyzed, or otherwise modified. AAs can exhibit an activatable conformation such that the AB is more accessible to a target after, for example, removal of the MM by cleavage, reduction, or photolysis of the CM in the presence of an agent capable of cleaving, reducing, or photolyzing the CM. However, a significant limitation of this art is the competition between the MM and the target for binding to the target binding moiety (TBM). Further, cleavage of the MM leads to significant off-target effects.

Another such probody is taught in U.S. Pat. No. 10,233, 244, issued to Sagert, et al., entitled, "Anti-ITGA3 antibodies, activatable anti-ITGA3 antibodies, and methods of use thereof". The invention is said to relate generally to antibodies that bind ITGa3, activatable antibodies that specifically bind to ITGa3 and methods of making and using these anti-ITGa3 antibodies and anti-ITGa3 activatable antibodies in a variety of therapeutic, diagnostic and prophylactic indications.

Another such probody is taught in U.S. Pat. No. 8,541, 203, issued to Daugherty, et al., entitled, "Activatable binding polypeptides and methods of identification and use thereof". These inventors teach activatable binding polypeptides (ABPs), which contain a target binding moiety (TBM), a masking moiety (MM), and a cleavable moiety (CM). The masking moiety covers the cognate binding site of the TBM, and the TBM is exposed upon cleavage of the CM. Certain activatable antibody compositions are said to include a TBM containing an antigen binding domain (ABD), a MM and a CM. The ABPs are said to include an "activatable" conformation such that at least one of the TBMs is less accessible to target when uncleaved than after cleavage of the CM in the presence of a cleaving agent capable of cleaving the CM. The application is said to teach libraries of candidate ABPs, methods of screening to identify such ABPs, and methods of use. ABPs specific for VEGF, CTLA-4, or VCAM are taught with ABPs having a first TBM that binds VEGF and a second TBM that binds FGF, as well as compositions and methods of use, at taught. Again, a significant limitation of this art is the competition between the MM and the target for binding to the TBM. Further, cleavage of the MM leads to significant off-target effects.

Another such probody is taught in U.S. Patent Publication No. 20190359714, filed by Tipton, et al., "Activatable Anti-CTLA-4 Antibodies and Uses Thereof". These applicants are said to teach activatable anti-human CTLA-4 antibodies comprising a heavy chain comprising a VH domain and a light chain comprising a masking moiety (MM), a cleavable moiety (CM), and a VL domain. Such activatable anti-human CTLA-4 antibodies have CTLA-4 binding activity in the tumor microenvironment, where the masking moiety is removed by proteolytic cleavage of the cleavable moiety by tumor-specific proteases, but exhibit greatly reduced binding to CTLA-4 outside the tumor.

Another such probody is taught in U.S. Patent Publication No. 20180271997, filed by Wang, entitled, "Methods and Reagents to Treat Tumor and Cancer". This applicant is said to teach reagents to treat tumor and cancer, and methods of using the same for treating tumor and cancer using a pro-antibody, which is antibody that can be activated in tumor. Another type of the reagent is said to be a conjugate of sialidase with affinity ligand that can bind to an immune cell surface or a conjugate of sialidase with affinity ligand that can bind to another antibody, therefore provide a sialidase based cancer immunotherapy.

Three approaches for activatable antibodies have been used to date. In the first, the probody includes a masking peptide linked via a proteolytic linker to block the antigen-antibody interaction. The development of each probody requires a screening process using phage display for a masking peptide. After cutting of linker, the masking peptide is expected to go away and release the antigen binding site of antibody. The problems with this approach include: (1) the heterogeneity of masking peptide itself induces immune responses; (2) the failure to release the masking peptide reduces efficacy; (3) some antigen-antibody interactions are too strong to be masked by a short (e.g., 10 amino acid) peptide; and (4) the peptides can be degraded before reaching to tumors and expose toxicity of antibodies to normal tissues.

In the second approach, Dual Variable Domain Immunoglobulins (DVD-Ig) are said to reduce the toxicity of anti-CTLA4 antibody. The VL and VH of an anti-TTA (Tumor Targeting Antigen) antibody are linked to the anti-CTLA-4 antibody via proteolytic linkers to cover the CTLA4 binding site. Unfortunately, this approach requires the pairing of the tumor associated antigen (TAA) and CTLA4, it requires adding an exact set of VL and VH, thus making the molecule bigger, and the exact VL and VH can always interact with off-target antigen and induce immune responses.

The third approach physically blocks the binding of an anti-CD3 variable light (VL) chain and a variable heavy (VH) by linking a "pseudo VL" and "pseudo VH" pair to an active and functional VL and VH. When pseudo VL interacts with VH, and when the pseudo VH interacts with VL, it does not have activity. Protease linkers are used to link together VL, VH, pseudo-VL and pseudo-VH, creating a very large molecule.

What is needed are novel fusion proteins that overcome the problems in the prior art, by eliminating targeting of normal tissues and enhancing the activity at the tumor target site.

SUMMARY OF THE INVENTION

In one embodiment, the present invention includes an activatable antibody (aAb) comprising, in order, the following structure: a first light chain comprising: a first variable light region; a cleavable linker; a first heavy chain comprising: a first variable heavy region; wherein the cleavable linker prevents or reduces the first light chain and the first heavy chain from forming a first antigen binding site against a first antigen; and wherein cleavage of the cleavable linker releases the first heavy chain to allow formation of the first antigen binding site to bind a first antigen. In one aspect, the aAb further comprises a second antibody binding site formed by a second variable light chain and a second constant light chain connected to the first heavy chain that binds a second antigen, and optionally a flexible non-cleavable linker between the second variable light chain and the second constant light chain. In another aspect, the aAb further comprises at least one of a first constant heavy region, a first constant heavy region, or both. In another aspect, the first light chain region, the first heavy chain region, or both, further comprise an Fc region, a wild-type Fc region, a mutated Fc region, a monomeric wild type Fc region, a monomeric mutant Fc region, a dimeric wild type Fc region, a dimeric mutant Fc region, a second variable heavy region and a second Fc region, or a second variable heavy region and a second Fc region and an uncleavable flexible linker and a second variable light region and a second heavy variable region, or a second Fc region and an uncleavable flexible linker and a cytokine. In another aspect, the first and second antigen are at least one of: the same antigen; the first and second antigen are different; or the first and second antigen is the same antigen but the first antigen binding site and the second antigen binding site bind different epitopes of the same antigen. In another aspect, the first antigen binding site or the second antigen binding site binds a tumor target. In another aspect, the first antigen is a tissue specific surface antigen selected from ICAM1; VCAMI; EpCAM; extra domain B of fibronectin; melanoma-associated chondroitin sulfate proteoglycan (MCSP); melanoma-associated proteoglycan (MAPG); high molecular weight melanoma associated antigen (HMV-MAA); prostate specific membrane antigen (PSMA); epidermal growth factor receptor (EGFR); hepatocyte growth factor receptor (HGFR); fibroblast activation protein (FAP); carcinoembryonic antigen (CEA); cell-adhesion molecule (CAM); human B-cell maturation target (BCMA); placental growth factor (PLGF); folate receptor, insulin-like growth factor receptor (ILGFR); CD133; CD40; CD37; CD33; CD30; CD28; CD24; CD23; CD22; CD21; CD20; CD19; CD13; CD10; HER3; HER2; nonmuscle myosin heavy chain type A (nmMHCA); transferrin; epithelial cell adhesion molecule (EpCAM); annexin A 1; nucleotin, tenascin, vascular endothelial growth factor receptor 1 (VEGFR1), vascular endothelial growth factor receptor 2; (VEGFR-2); aminopeptidase N, tie-1, tie-2, or c-Met. In another aspect, the first antigen is selected from a protein, a portion of a protein, or a peptides encoded by at least one gene selected from: ABCF1; ACVRI; ACVRIB; ACVR2; ACVR2B;

ACVRLI; ADORA2A; Aggrecan; AGR2; AICDA; AIF1; AIG1; AKAPI; AKAP2; AMH; AMHR2; ANGPTI; ANGPT2; ANGPTL3; ANGPTL4; ANPEP; APC; APOCI; AR; AZGP1; B7.1; B7.2; BAD; BAFF; BAG1; BAII; BCL2; BCL6; BDNF; BLNK; BLR1 (MDR15); BlyS; BMP1; BMP2; BMP3B (GDF10); BMP4; BMP6; BMP8; BMPRIA; BMPRIB; BMPR2; BPAGI (plectin); BRCA1; C19orf10 (IL27w); C3; C4A; C5; C5R1; CANTI; CASPI; CASP4; CAVI; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-la); CCL4 (MIP-lb); CCL5 (RANTES); CCL7 (MCP-3); CCL8 (mcp-2); CCNA1; CCNA2; CCNDI; CCNEI; CCNE2; CCR1 (CKR1/HM145); CCR2 (mcp-1RB/RA); CCR3 (CKR3/CMKBR3); CCR4; CCR5 (CMKBR5/ChemR 13); CCR6 (CMKBR6/CKR-L3/STRL22/DRY6); CCR7 (CKR7/EBI1); CCR8 (CMKBR8/TER1/CKR-L1); CCR9 (GPR-9-6); CCRLI (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/Cipl); CDKNIB (p27Kipl); CDKNIC; CDKN2A (p16INK4a); CDKN2B; CDKN2C; CDKN3; CEBPB; CERI; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CXCLIO (IP-IO); CXCL11 (I-TAC/IP-9); CXCL12 (SDF1); CXCL13; CXCL14; CXCL16; CXCL2 (GR02); CXCL3 (GR03); CXCL5 (ENA-78/LIX); CXCL6 (GCP-2); CXCL9 (MIG); CXCR3 (GPR9/CKR-L2); CXCR4; CXCR6 (TYM-STR/STRL33/Bonzo); CYB5; CYC1; CYSLTRI; CGRP; Clq; Clr; CI; C4a; C4b; C2a; C2b; C3a; C3b; DAB2IP; DES; DKFZp451J0118; DNCL1; DPP4; E-selectin; E2F1; ECGF1; EDG1; EFNA1; EFNA3; EFNB2; EGF; EGFR; ELAC2; ENG; ENOI; EN02; EN03; EPHB4; EPO; ERBB2 (Her-2); EREG; ERK8; ESR1; ESR2; F3 (TF); Factor VII; Factor IX; Factor V; Factor Vila; Factor X; Factor XII; Factor XIII; FADD; FasL; FASN; FCERIA; FCER2; Fc gamma receptor; FCGR3A; FGF; FGFI (aFGF); FGF10; FGFII; FGF12; FGF12B; FGF1 3; FGF1 4; FGF16; FGF1 7; FGF1 8; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FILI (EPSILON); FILI (ZETA); FLJ12584; FLJ25530; FLRTI (fibronectin); FLTI; FOS; FOSLI (FRA-1); FY (DARC); GABRP (GABAa); GAGEBI; GAGECI; GALNAC4S-6ST; GATA3; GDF5; GFII; GGTI; GMCSF; GNAS1; GNRH1; GPR2 (CCR10); GPR31; GPR44; GPR81 (FKSG80); GRCC10 (CIO); GRP; GSN (Gelsolin); GSTP1; glycoprotein (GP) Ilb/IIIa; HAVCR2; HDAC4; HDAC5; HDAC7A; HDAC9; Her2; HGF; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRTI; KRT19 (Keratin 19); KRT2A; KRTHB6 (hair-specific type II keratin); L-selectin; LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB 1; midkine; MIF; MIP-2; MKI67 (Ki-67);

MMP2; MMP9; MS4A1; MSMB; MT3 (metallothionectin-III); MTSSI; MUCI (mucin); MYC; MYD88; NCK2; neurocan; NKG2D; NFKB1; NFKB2; NGF; NGFB (NGF); NGFR; NgR-Lingo; NgR-Nogo66 (Nogo); NgR-p75; NgR-Troy; NME1 (NM23A); NOX5; NPPB; NROB1; NROB2; NRID1; NRID2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRDI; P2RX7; PAP; PARTI; PATE; PAWR; PCA3; PCNA; PDGFA; PDGFB; PECAMI; PF4 (CXCL4); PGE2; PGF; PGR; phosphacan; PIAS2; PIK3CG; plasminogen activator; PLAU (uPA); PLG; PLXDC1; PPBP (CXCL7); PPID; PRI; PRKCQ; PRKDI; PRL; PROC; Protein C; PROK2; PSAP; PSCA; PTAFR; PTEN; PTGS2 (COX-2); PTN; RAC2 (p21Rac2); RAGE; RARB; RGSI; RGS13; RGS3; RNFIIO (ZNF144); ROB02; SI00A2; SCGBID2 (lipophilin B); SCGB2A1 (mammaglobin 2); SCGB2A2 (mammaglobin 1); SCYEI (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRRIB (Sprl); ST6GAL1; STABI; STAT6; STEAP; STEAP2; substance P; TB4R2; TBX21; TCP10; TDGF1; TEK; TGFA; TGFB1; TGFB111; TGFB2; TGFB3; TGFBI; TGFBR1; TGFBR2; TGFBR3; THIL; THBSI (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-α; TNFAIP2 (B94); TNFAIP3; TNFRSF11A; TNFRSFIA; TNFRSF1B; TNFRSF21; TNFRSF5; TNFRSF6 (Fas); TNFRSF7; TNFRSF8; TNFRSF9; TNFSFIO (TRAIL); TNFSF11 (TRANCE); TNFSF12 (AP03L); TNFSF13 (April); TNFSF13B; TNFSF14 (HVEML); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM1; TPM2; TRADD; TRAFI; TRAF2; TRAF3; TRAF4; TRAF5; TRAF6; TREMI; TREM2; TRPC6; TSLP; TWEAK; thrombomodulin; thrombin; VEGF; VEGFB; VEGFC; versican; VHL C5; VLA-4; XCLI (lymphotactin); XCL2 (SCM-1b); XCR1 (GPR5/CCXCR1); YY1; and ZFPM2. In another aspect, the tumor target is selected from a tumor targeting antigen, HER1, HER2, HER3, GD2, carcinoembryonic antigens (CEAs), epidermal growth factor receptor active mutant (EGFRVIII), CD133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUCI, prostate stem cell antigen (PSCA), Wilms tumor-1 (WT-1), or a Claudin family protein. In another aspect, the first antigen binding site or the second antigen binding site binds a T-cell marker. In another aspect, the T-cell marker is selected from CTLA-4, PD-1, Lag3, S15, B7H3, B7H4, TCR-alpha, TCR-beta, or TIM-3. In another aspect, the first antigen binding site or the second antigen binding site binds a T-cell activator. In another aspect, the T-cell activator is selected from CD3, 41BB or OX40. In another aspect, the cleavable linker is a protease cleavable linker. In another aspect, the cleavable linker is cleaved by a tumor associated protease: MMP1, MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B. In another aspect, the cleavable linker is cleaved by proteases upregulated during apoptosis or inflammation associated responses. In another aspect, the cleavable linker is cleaved by a caspase. In another aspect, the caspase is Caspase 1, Caspase 2, Caspase 3, Caspase 4, Caspase 5, Caspase 6, Caspase 7, Caspase 8, Caspase 9, Caspase 10, Caspase 11 and Caspase 12. In another aspect, the cleavable linker does not mask an antigen binding site. In another aspect, the aAb further comprises an agent conjugated to the aAb. In another aspect, the aAb further comprises a cytokine attached to, or in a fusion protein with the aAb or an Fc region. In another aspect, the cytokine is selected from at least one of: growth hormone; parathyroid hormone; thyroxine; insulin; proinsulin; relaxin; prorelaxin; glycoprotein hormones; hepatic growth factor; fibroblast growth factor; prolactin; placental lactogen; TNF-α; mullerian-inhibiting substance; gonadotropin-associated peptide; inhibin; activin; vascular endothelial growth factor; integrin; thrombopoietin (TPO); nerve growth factors; platelet-growth factor; placental growth factor, transforming growth factors (TGFs); insulin-like growth factor-1 and -11; erythropoietin (EPO); osteoinductive factors; interferons; colony stimulating factors (CSFs); lymphotoxin-alpha; lymphotoxin-beta; CD27L; CD30L; FASL; 4-1 BBL; OX40L; TRAIL; IL-1; IL-2; IL-3; IL-4; IL-5; IL-6; IL-7; IL-8; IL-9; IL-10; IL-11; IL-12; IL-13; IL-15; IL-18; IL-21; IL-22; IL-23; IL-33; IFN-α; IFN-b; IFN-g; IFN-g inducing factor (IGIF); bone morphogenetic protein (BMP); leukemia inhibitory factor (LIF); or kit ligand (KL). In another aspect, the aAb has is selected from SEQ ID NOS: 1, 2, or 3. In another aspect, the agent is at least one of: a toxin or toxic fragment thereof; a microtubule inhibitor; a nucleic acid damaging agent; a detectable moiety; or a diagnostic agent.

In another embodiment, the present invention includes a pharmaceutical composition comprising the activatable Ab. In another embodiment, the present invention includes a method of reducing binding activity of an activatable Ab against normal tissues and targeting a cancer cell comprising administering an effective amount of the activatable Ab to a subject in need thereof. In another embodiment, the present invention includes a method of treating, alleviating a symptom of, or delaying the progression of a cancer comprising administering an effective amount of the activatable Ab a subject in need thereof. In one aspect, the cancer is a cancer that expresses an enzyme that cleaves the cleavable linker. In another aspect, the cancer is selected from a bladder cancer, a bone cancer, a breast cancer, a carcinoid, a cervical cancer, a colon cancer, an endometrial cancer, a glioma, a head and neck cancer, a liver cancer, a lung cancer, a lymphoma, a melanoma, an ovarian cancer, a pancreatic cancer, a prostate cancer, a renal cancer, a sarcoma, a skin cancer, a stomach cancer, a testis cancer, a thyroid cancer, a urogenital cancer, or a urothelial cancer. In another aspect, the cancer is selected from the group consisting of: acute myeloid leukemia, adrenocortical carcinoma, B-cell lymphoma, bladder urothelial carcinoma, breast ductal carcinoma, breast lobular carcinoma, carcinomas of the esophagus, castration-resistant prostate cancer (CRPC), cervical carcinoma, cholangiocarcinoma, chronic myelogenous leukemia, colorectal adenocarcinoma, colorectal cancer (CRC), esophageal carcinoma, gastric adenocarcinoma, glioblastoma multiforme, head and neck squamous cell carcinoma, Hodgkin's lymphoma/primary mediastinal B-cell lymphoma, hepatocellular carcinoma (HCC), kidney chromophobe carcinoma, kidney clear cell carcinoma, kidney papillary cell carcinoma, lower grade glioma, lung adenocarcinoma, lung aquamous cell carcinoma, melanoma (MEL), mesothelioma, non-squamous NSCLC, ovarian serous adenocarcinoma, pancreatic ductal adenocarcinoma, paraganglioma & pheochromocytoma, prostate adenocarcinoma, renal cell carcinoma (RCC), sarcoma, skin cutaneous melanoma, squamous cell carcinoma of the head and neck, T-cell lymphoma, thymoma, thyroid papillary carcinoma, uterine carcinosarcoma, uterine corpus endometrioid carcinoma and uveal melanoma.

In another embodiment, the present invention includes an activatable antibody (aAb) comprising, in order, the following structure: a first light chain comprising a first variable light region; a cleavable linker; a first heavy chain comprising a first variable heavy region; and wherein the cleavable linker prevents or reduces the first light chain and the first heavy chain from forming an antigen binding site against a first antigen; wherein cleavage of the cleavable linker releases the first heavy chain to form an antibody binding site with the first light chain that binds a first antigen. In another aspect, the aAb further comprises at least one of a first constant light region or a first constant heavy region, respectively. In another aspect, the aAb further comprises an Fc region attached to a first constant heavy region, wherein the Fc region is a wild-type or a mutant domain that modifies Fc receptor binding, a second variable heavy region and a second Fc region, or a second variable heavy region and a second Fc region and an uncleavable flexible linker and a second variable light region and a second heavy variable region, or a second Fc region and an uncleavable flexible linker and a cytokine. In another aspect, the aAb further comprises a second antibody binding site formed by a second variable light chain and a second constant light chain connected to the first heavy chain that binds a second antigen, and optionally a flexible non-cleavable linker between the second variable light chain and the second constant light chain. In another aspect, the aAb further comprises at least one of a first constant heavy region, a first constant heavy region, or both. In another aspect, the Fc region is a wild-type Fc region, a mutated Fc region, a monomeric wild type Fc region, a monomeric mutant Fc region, a dimeric wild type Fc region, or a dimeric mutant Fc region. In another aspect, the aAb further comprises a cytokine attached to, or in a fusion protein with the aAb or the Fc region. In another aspect, the cytokine is selected from at least one of: growth hormone; parathyroid hormone; thyroxine; insulin; proinsulin; relaxin; prorelaxin; glycoprotein hormones; hepatic growth factor; fibroblast growth factor; prolactin; placental lactogen; TNF-alpha; mullerian-inhibiting substance; gonadotropin-associated peptide; inhibin; activin; vascular endothelial growth factor; integrin; thrombopoietin (TPO); nerve growth factors; platelet-growth factor; placental growth factor, transforming growth factors (TGFs); insulin-like growth factor-1 and -11; erythropoietin (EPO); osteoinductive factors; interferons; colony stimulating factors (CSFs); lymphotoxin-alpha; lymphotoxin-beta; CD27L; CD30L; FASL; 4-1 BBL; OX40L; TRAIL; IL-1; IL-2; IL-3; IL-4; IL-5; IL-6; IL-7; IL-8; IL-9; IL-10; IL-11; IL-12; IL-13; IL-15; IL-18; IL-21; IL-22; IL-23; IL-33; IFN-a; IFN-beta; IFN-gamma; IFN-gamma inducing factor (IGIF); bone morphogenetic protein (BMP); leukemia inhibitory factor (LIF); or kit ligand (KL). In another aspect, the first antigen is a tissue specific surface antigen selected from ICAMI; VCAMI; EpCAM; extra domain B of fibronectin; melanoma-associated chondroitin sulfate proteoglycan (MCSP); melanoma-associated proteoglycan (MAPG); high molecular weight melanoma associated antigen (HMV-MAA); prostate specific membrane antigen (PSMA); epidermal growth factor receptor (EGFR); hepatocyte growth factor receptor (HGFR); fibroblast activation protein (FAP); carcinoembryonic antigen (CEA);

cell-adhesion molecule (CAM); human B-cell maturation target (BCMA); placental growth factor (PLGF); folate receptor, insulin-like growth factor receptor (ILGFR); CD133; CD40; CD37; CD33; CD30; CD28; CD24; CD23; CD22; CD21; CD20; CD19; CD13; CD10; HER3; HER2; nonmuscle myosin heavy chain type A (nmMHCA); transferrin; epithelial cell adhesion molecule (EpCAM); annexin A 1; nucleotin, tenascin, vascular endothelial growth factor receptor 1 (VEGFR1), vascular endothelial growth factor receptor 2; (VEGFR-2); aminopeptidase N, tie-1, tie-2, or c-Met. In another aspect, the first antigen is selected from a protein, a portion of a protein, or a peptides encoded by at least one gene selected from: ABCF1; ACVR1; ACVRIB; ACVR2; ACVR2B; ACVRLI; ADORA2A; aggrecan; AGR2; AICDA; AIFI; AIGI; AKAPI; AKAP2; AMH; AMHR2; ANGPTI; ANGPT2; ANGPTL3; ANGPTL4; ANPEP; APC; APOC1; AR; AZGP1 (zinc-a-glycoprotein); B7.1; B7.2; BAD; BAFF; BAGI; BAII; BCL2; BCL6; BDNF; BLNK; BLR1 (MDR15); BlyS; BMP1; BMP2; BMP3B (GDF10); BMP4; BMP6; BMP8; BMPRIA; BMPRIB; BMPR2; BPAGI (plectin); BRCA1; C19orf10 (IL27w); C3; C4A; C5; C5R1; CANTI; CASPI; CASP4; CAVI; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-la); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRLI (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/Cipl); CDKNIB (p27Kipl); CDKNIC; CDKN2A (pl6INK4a); CDKN2B; CDKN2C; CDKN3; CEBPB; CER1; CHGA; CHGB; chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CXCLIO (IP-IO); CXCL11 (I-TAC/IP-9); CXCL12 (SDF1); CXCL13; CXCL14; CXCL16; CXCL2 (GR02); CXCL3 (GR03); CXCL5 (ENA-78/LIX); CXCL6 (GCP-2); CXCL9 (MIG); CXCR3 (GPR9/CKR-L2); CXCR4; CXCR6 (TYM-STR/STRL33/Bonzo); CYB5; CYC1; CYSLTRI; CGRP; Clq; CIR protein; CI; C4a; C4b; C2a; C2b; C3a; C3b; DAB2IP; DES; DKFZp451J0118; DNCLI; DPP4; E-selectin; E2F1; ECGF1; EDG1; EFNA1; EFNA3; EFNB2; EGF; EGFR; ELAC2; ENG; ENOI; EN02; EN03; EPHB4; EPO; ERBB2 (Her-2); EREG; ERK8; ESR1; ESR2; F3 (TF); Factor VII; Factor IX; Factor V; Factor VIIa; Factor X; Factor XII; Factor XIII; FADD; FasL; FASN; FCERIA; FCER2; Fc gamma receptor; FCGR3A; FGF; FGFI (aFGF); FGF10; FGF11; FGF12; FGF12B; FGF1 3; FGF1 4; FGF16; Fgfl7; Fgfl 8; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FILI (EPSILON); FILI (ZETA); FLJ12584; FLJ25530; FLRTI (fibronectin); FLTI; FOS; FOSLI (FRA- 1); FY (DARC); GABRP (GABAa); GAGEBI; GAGECI; GALNAC4S-6ST; GATA3; GDF5; GFII; GGTI; GMCSF; GNAS1; GNRH1; GPR2 (CCR10); GPR31; GPR44; GPR81 (FKSG80); GRCC10 (CIO); GRP; GSN (Gelsolin); GSTP1; glycoprotein IIb; glycoprotein IIIa; HAVCR2; HDAC4; HDAC5; HDAC7A; HDAC9; Her2; HGF; HIFIA; HIP1; histamine and histamine receptors; HLA-A; HLA-DRA; HM74; HMGB1; HMOX1; HUMCYT2A; ICE-BERG; ICOSL; ID2; IFN-alpha; IFNA1; IFNA2; IFNA4; IFNA5; IFNA6; IFNA7; IFNB1; IFN-gamma; IFNW1; IGBP1; IGF1; IGFIR; IGF2; IGFBP2; IGFBP3; IGFBP6; IL-1; ILIA; ILIB; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; ILIA; ILIB; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAKI; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); L-selectin; *LAMA5*; LEP (leptin); Lingo-p75; Lingo-Troy; LPS; LTA (TNF-b); LTB; LTB4R (GPR16); LTB4R2; LTBR; MAC-MARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSSI; MUCI (mucin); MYC; MYD88; NCK2; neurocan; NKG2D; NFKB1; NFKB2; NGF; NGFB (NGF); NGFR; NgR-Lingo; NgR-Nogo66 (Nogo); NgR-p75; NgR-Troy; NME1 (NM23A); NOX5; NPPB; NROB1; NROB2; NRID1; NRID2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRDI; P2RX7; PAP; PARTI; PATE; PAWR; PCA3; PCNA; PDGFA; PDGFB; PECAMI; PF4 (CXCL4); PGE2; PGF; PGR; phosphacan; PIAS2; PIK3CG; plasmi-nogen activator; PLAU (uPA); PLG; PLXDC1; PPBP (CXCL7); PPID; PRI; PRKCQ; PRKDI; PRL; PROC; Pro-tein C; PROK2; PSAP; PSCA; PTAFR; PTEN; PTGS2 (COX-2); PTN; RAC2 (p21Rac2); RAGE; RARB; RGSI; RGS13; RGS3; RNFIIO (ZNF144); ROB02; SI00A2; SCGB1D2 (lipophilin B); SCGB2A1 (mammaglobin 2); SCGB2A2 (mammaglobin 1); SCYEI (endothelial Mono-cyte-activating cytokine); SDF2; SERPINA1; SERPINA3; SERPINB5 (maspin); SERPINEI (PAI-1); SERPINF1; SHBG; SLA2; SLC2A2; SLC33A1; SLC43A1; SLIT2; SPP1; SPRR1B (Sprl); ST6GAL1; STAB1; STAT6; STEAP; STEAP2; substance P; TB4R2; TBX21; TCP10; TDGF1; TEK; TGFA; TGFB1; TGFB111; TGFB2; TGFB3; TGFB1; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF-alpha; TNFAIP2 (B94); TNFAIP3; TNFRSF11A; TNFRSFIA; TNFRSF1B; TNFRSF21; TNFRSF5; TNFRSF6 (Fas); TNFRSF7; TNFRSF8; TNFRSF9; TNFSFIO (TRAIL); TNFSF11 (TRANCE); TNFSF12 (AP03L); TNFSF13 (April); TNFSF13B; TNFSF14 (HVEML); TNFSF15 (VEGI);

TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM1; TPM2; TRADD; TRAFI; TRAF2; TRAF3; TRAF4; TRAF5; TRAF6; TREMI; TREM2; TRPC6; TSLP; TWEAK; throm-bomodulin; thrombin; VEGF; VEGFB; VEGFC; versican; VHL C5; VLA-4; XCL1 (lymphotactin); XCL2 (SCM-1b); XCR1 (GPR5/CCXCR1); YY1; and ZFPM2. In another aspect, the first and second antigen are at least one of: the same antigen; the first and second antigen are different; or the first and second antigen is the same antigen but the first antigen binding site and the second antigen binding site bind different epitopes of the same antigen. In another aspect, the first antigen binding site or the second antigen binding site binds a tumor target. In another aspect, the tumor target is selected from a tumor targeting antigen, HER1, HER2, HER3, GD2, carcinoembryonic antigens (CEAs), epidermal growth factor receptor active mutant (EGFRVIII), CD133, fibroblast Activation Protein Alpha (FAP), epithelial cell adhesion molecular (Epcam), glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUCI, prostate stem cell antigen (PSCA), Wilms tumor-1 (WT-1), or a Claudin family mem-ber. In another aspect, the first antigen binding site or the second antigen binding site binds a T-cell marker. In another aspect, the T-cell marker is selected from CTLA-4, PD-1, Lag3, S15, B7H3, B7H4, TCR-alpha, TCR-beta, TIM-3. In another aspect, the first antigen binding site or the second antigen binding site binds a T-cell activator. In another aspect, the T-cell activator is selected from CD3, 41BB or OX40. In another aspect, the cleavable linker is a protease cleavable linker. In another aspect, the cleavable linker is cleaved by a tumor associated protease: MMPI, MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B. In another aspect, the cleavable linker is cleaved by proteases upregu-lated during apoptosis or inflammation associated responses. In another aspect, the cleavable linker is cleaved by a caspase. In another aspect, the caspase is Caspase 1, Caspase 2, Caspase 3, Caspase 4, Caspase 5, Caspase 6, Caspase 7, Caspase 8, Caspase 9, Caspase 10, Caspase 11 and Caspase 12. In another aspect, the cleavable linker does not mask an antigen binding site. In another aspect, the aAb further comprises an agent conjugated to the aAb. In another aspect, the agent is at least one of: a toxin or toxic fragment thereof; a microtubule inhibitor; a nucleic acid damaging agent; a detectable moiety; or a diagnostic agent. In another aspect, the aAb has is selected from SEQ ID NOS: 1, 2, or 3.

In another embodiment, the present invention includes a nucleic acid that encodes an activatable antibody (aAb) that includes, in order, the following structure: a first light chain comprising: a first variable light region; a cleavable linker; a first heavy chain comprising: a first variable heavy region; wherein the cleavable linker prevents or reduces the first light chain and the first heavy chain from forming a first antigen binding site against a first antigen; and wherein cleavage of the cleavable linker releases the first heavy chain to allow formation of the first antigen binding site to bind a first antigen.

In another embodiment, the present invention includes a nucleic acid that encodes an activatable antibody (aAb) that includes, in order, the following structure: a first light chain comprising a first variable light region; a cleavable linker; a first heavy chain comprising a first variable heavy region;

and wherein the cleavable linker prevents or reduces the first light chain and the first heavy chain from forming an antigen binding site against a first antigen; wherein cleavage of the cleavable linker releases the first heavy chain to form an antibody binding site with the first light chain that binds a first antigen.

In another embodiment, the present invention includes a cell that comprises a nucleic acid that encodes an activatable antibody (aAb) that includes, in order, the following structure: a first light chain comprising: a first variable light region; a cleavable linker; a first heavy chain comprising: a first variable heavy region; wherein the cleavable linker prevents or reduces the first light chain and the first heavy chain from forming a first antigen binding site against a first antigen; and wherein cleavage of the cleavable linker releases the first heavy chain to allow formation of the first antigen binding site to bind a first antigen.

In another embodiment, the present invention includes a cell that comprises a nucleic acid that encodes an activatable antibody (aAb) that includes, in order, the following structure: a first light chain comprising a first variable light region; a cleavable linker; a first heavy chain comprising a first variable heavy region; and wherein the cleavable linker prevents or reduces the first light chain and the first heavy chain from forming an antigen binding site against a first antigen; wherein cleavage of the cleavable linker releases the first heavy chain to form an antibody binding site with the first light chain that binds a first antigen.

In another embodiment, the present invention includes a pharmaceutical composition comprising the activatable Ab and a carrier. In another embodiment, the present invention includes a method of reducing binding activity of an antibody against normal tissues and targeting a cancer cell comprising administering an effective amount of the activatable Ab to a subject in need thereof.

In another embodiment, the present invention includes a method of treating, alleviating a symptom of, or delaying the progression of a cancer comprising administering an effective amount of the activatable Ab to a subject in need thereof. In one aspect, the cancer is a cancer that expresses an enzyme that cleaves the cleavable linker. In another aspect, the cancer is selected from a bladder cancer, a bone cancer, a breast cancer, a carcinoid, a cervical cancer, a colon cancer, an endometrial cancer, a glioma, a head and neck cancer, a liver cancer, a lung cancer, a lymphoma, a melanoma, an ovarian cancer, a pancreatic cancer, a prostate cancer, a renal cancer, a sarcoma, a skin cancer, a stomach cancer, a testis cancer, a thyroid cancer, a urogenital cancer, or a urothelial cancer. In another aspect, the cancer is selected from the group consisting of acute myeloid leukemia, adrenocortical carcinoma, B-cell lymphoma, bladder urothelial carcinoma, breast ductal carcinoma, breast lobular carcinoma, carcinomas of the esophagus, castration-resistant prostate cancer (CRPC), cervical carcinoma, cholangiocarcinoma, chronic myelogenous leukemia, colorectal adenocarcinoma, colorectal cancer (CRC), esophageal carcinoma, gastric adenocarcinoma, glioblastoma multiforme, head and neck squamous cell carcinoma, Hodgkin's lymphoma/primary mediastinal B-cell lymphoma, hepatocellular carcinoma (HCC), kidney chromophobe carcinoma, kidney clear cell carcinoma, kidney papillary cell carcinoma, lower grade glioma, lung adenocarcinoma, lung aquamous cell carcinoma, melanoma (MEL), mesothelioma, non-squamous NSCLC, ovarian serous adenocarcinoma, pancreatic ductal adenocarcinoma, paraganglioma & pheochromocytoma, prostate adenocarcinoma, renal cell carcinoma (RCC), sarcoma, skin cutaneous melanoma, squamous cell carcinoma of the head and neck, T-cell lymphoma, thymoma, thyroid papillary carcinoma, uterine carcinosarcoma, uterine corpus endometrioid carcinoma and uveal melanoma.

In another embodiment, the present invention includes an activatable Antibody (aAb), in order, comprising: a first variable light region; a cleavable linker; and a first variable heavy region; and an Fc region; wherein the cleavable linker prevents the first variable light region and the first variable heavy region from forming a first antigen binding site against a first antigen, wherein the cleavable linker does not mask the antigen binding site; and wherein cleavage of the cleavable linker releases the first variable heavy region to allow formation of the first antigen binding site that binds a first antigen.

In another embodiment, the present invention includes a cell that expresses an activatable antibody (aAb) comprising, in order, the following structure: a first light chain comprising: a first variable light region; a cleavable linker; a first heavy chain comprising: a first variable heavy region; wherein the cleavable linker prevents or reduces the first light chain and the first heavy chain from forming a first antigen binding site against a first antigen; and wherein cleavage of the cleavable linker releases the first heavy chain to allow formation of the first antigen binding site to bind a first antigen. In one aspect, the cell is a T cell or a mesenchymal stem cell. In another aspect, the aAb further comprises a transmembrane sequence that anchors the aAb to the surface of a T cell to form a chimeric antigen receptor, wherein the cell is a CAR T cell.

BRIEF DESCRIPTION OF THE DRAWINGS

For a more complete understanding of the features and advantages of the present invention, reference is now made to the detailed description of the invention along with the accompanying figures and in which:

FIG. 1A. The schematics of AABs. FIG. 1B shows the first type of antigen binding activation. CL and VH is linked with a proteolytic linker sensitive to MMP14. VH is not able to pair with VL to form a stable antigen binding site before cutting. VH is released after cutting with MMP14 and is able to pair with VL to form the antigen binding site. FIG. 1C shows the second type of antigen binding activation. The first Fc and VH is linked with a proteolytic linker sensitive to MMP14. VH is not able to pair with VL to form a stable antigen binding site before cutting. VH is released after cutting with MMP14 and is able to pair with VL to form the antigen binding site.

DETAILED DESCRIPTION OF THE INVENTION

Figure 1A:
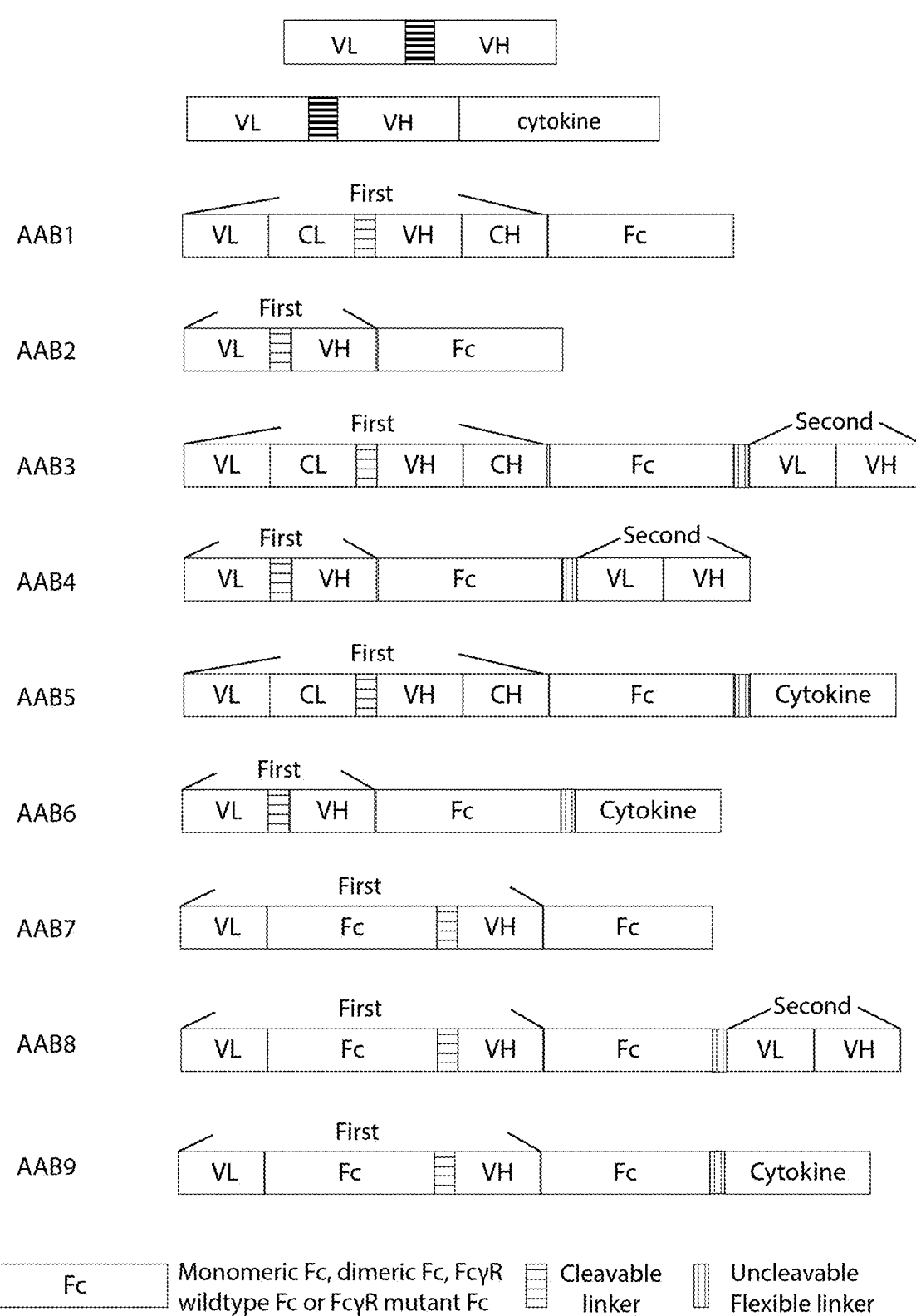
FIGS. 1A-1C show_schematic diagrams of proteins and diagrams to show how Pro antibody designs regains the antigen binding ability after cutting.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

Therapeutic monoclonal antibodies have been developed to treat a variety of human diseases including cancer. In cancer therapy, for example, anti-CTLA4 antibody or anti-CD3 antibodies have been used to activate T cells via reducing the immunosuppression signal in tumor microenvironment. However, systemic T cell over activation due to off-target Ag-Ab interactions leads to significant adverse events. Antibodies against tumor-associated antigens (TAA) often targets non-tumor tissues that express the same antigens. In the case of anti-CTLA4 activatable antibodies of the prior art, the constructs add both synthetic/foreign extraneous peptides (the masking moiety) in addition to cleavable linkers to block the activity of anti-CTLA-4. These two extra peptides can lead to an immune response to the linker, and further, cleavage of the linker does not ensure release of the masking moiety from the antigen binding site.

The present invention reduces off-target toxicities for monoclonal antibody therapies, thereby increasing the therapeutic index and drug tolerability for patients, by eliminating the use of a masking moiety. It was found that the pro-antibodies taught herein have little to no activity until the drug reaches the tumor, thus yielding a long half-life, protein stability and manufacturability. The new pro-antibodies are designed to shorten heavy and light chains of antibody with a short linker that reduces binding to the targeting molecules. Since this short linker is sensitive to tumor associated proteases, when the linker is cut it restores the topologic position of heavy and light chains and therefore its binding affinity to the target at tumor tissues.

As used herein, the term "activatable antibodies", "aAb", "pro-antibody", or "probody" refers to a fusion protein that includes antibody antigen binding domains that are separated by a cleavable linker. The basic structure of the fusion protein includes, from amino to carboxy: a variable light region-cleavable linker-variable heavy region or a variable heavy region-cleavable linker-variable light region. The first fusion protein can be co-expressed with a second fusion protein that targets a second antigen, while the first fusion protein binds a first antigen. The first and second antigens can be the same antigen, a different antigen, or even the same antigen but bind a different epitope of the antigen. The fusion protein may also include one or more of the following: the constant light region, the constant heavy region, Fc region (wild-type or mutant), a second linker between the Fc and a second protein (e.g., a cytokine).

A nucleic acid encoding the aAb can be part of a vector that is used to express the aAb in a host cell, such as a bacterial, fungal, plant, or mammalian cell.

As used herein, the terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab') 2, Fv, and single-chain variable fragment (scFv) antibodies. An antibody other than a "bispecific" or "bifunctional" antibody is understood to have identical binding sites. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

As used herein, the term "bispecific" or "bifunctional" antibody is understood to have two different antigen binding sites. For example, the bispecific antibody of the present invention will include two different antigen binding domains, e.g., a first and a second antigen binding domain that each binds a first and a second antigen, respectively. The bispecific antibody can also have two different antigen binding regions that bind the same antigen, but at two different epitopes. More commonly, the bispecific antibody will bind two different antigens. The first or second antigen will generally be a tumor specific antigen, while the other antigen binding region with bind a T cell activating molecule on a T cell.

As used herein, the term "antibody" is used in the broadest sense, and specifically covers monoclonal antibodies (including full length antibodies or other bivalent, Fc-region containing antibodies such as bivalent scFv Fc-fusion antibodies), polyclonal antibodies, multispecific antibodies (e.g., bispecific antibodies), and antibody fragments (e.g., Fab, Fab', $F(ab')_2$, Fv, scFv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. The present invention includes monoclonal antibodies (and binding fragments thereof) that are completely recombinant, in other words, where the complementarity determining regions (CDRs) are genetically spliced into a human antibody backbone, often referred to as veneering an antibody. Thus, in certain aspects the monoclonal antibody is a fully synthesized antibody. In certain embodiments, the monoclonal antibodies (and binding fragments thereof) can be made in bacterial or eukaryotic cells, including plant cells.

As used herein, the term "antibody fragment" refers to a portion of a full-length antibody, generally the antigen binding or variable region and include Fab, Fab', $F(ab')_2$, Fv and scFv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F $(ab')_2$ fragment that has two antigen binding fragments which are capable of cross-linking antigen, and a residual other fragment (which is termed pFc'). As used herein, "functional fragment" with respect to antibodies, refers to Fv, F (ab) and $F(ab')_2$ fragments.

As used herein, the "Fv" fragment is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment, also designated as F (ab), also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the $F(ab')_2$ pepsin digestion product. Additional chemical couplings of antibody fragments are known to those of ordinary skill in the art.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond. While the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82 4592-4596 (1985), relevant portions incorporated herein by reference.

As used herein, an "isolated" antibody is one that has been identified and separated and/or recovered from a component of the environment in which it was produced. Contaminant components of its production environment are materials, which would interfere with diagnostic or therapeutic uses for the antibody, and may include enzymes, hormones, and other proteinaceous or nonproteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spinning cup sequentator, such as at least 15 residues of sequence; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95, 96, 97, 98, or 99%.

As used herein, the term "variable" in the context of variable domain of antibodies, refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), Nature 342: 877), or both, that is Chothia plus Kabat. The more highly conserved portions of variable domains are called the framework (FR). The variable domains of native heavy and light chains each comprise four FR regions, largely adopting a B-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al.) The constant domains are not involved directly in binding an antibody to an antigen, but exhibit various effector function, such as participation of the antibody in antibody-dependent cellular toxicity.

The light chains of antibodies (immunoglobulin) from any vertebrate species can be assigned to one of two clearly distinct types, called kappa and lambda, based on the amino sequences of their constant domain.

Depending on the amino acid sequences of the constant domain of their heavy chains, "immunoglobulins" can be assigned to different classes. There are at least five (5) major classes of immunoglobulins: IgA, IgD, IgE, IgG and IgM, and several of these may be further divided into subclasses (isotypes), e.g., IgG-1, IgG-2, IgG-3 and IgG4; IgA-1 and IgA-2. The subunit structures and three-dimensional configurations of different classes of immunoglobulins are well known.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed and claimed invention may be made by the hybridoma method first described by Kohler and Milstein, Nature 256, 495 (1975), relevant portions incorporated herein by reference.

All monoclonal antibodies utilized in accordance with the presently disclosed and claimed invention will be either (1) the result of a deliberate immunization protocol, as described in more detail herein below; or (2) the result of an immune response that results in the production of antibodies naturally in the course of a disease or cancer.

The uses of the monoclonal antibodies of the presently disclosed and claimed invention may require administration of such or similar monoclonal antibody to a subject, such as a human. However, when the monoclonal antibodies are produced in a non-human animal, such as a rodent or chicken, administration of such antibodies to a human patient will normally elicit an immune response, wherein the immune response is directed towards the antibodies themselves. Such reactions limit the duration and effectiveness of such a therapy. In order to overcome such problem, the monoclonal antibodies of the presently disclosed and claimed invention can be "humanized", that is, the antibodies are engineered such that antigenic portions thereof are removed and like portions of a human antibody are substituted therefore, while the antibodies' affinity for a specific antigen is retained. This engineering may only involve a few amino acids, or may include entire framework regions of the antibody, leaving only the complementarity determining regions of the antibody intact. Several methods of humanizing antibodies are known in the art and are disclosed in U.S. Pat. No. 6,180,370, issued to Queen et al on Jan. 30, 2001; U.S. Pat. No. 6,054,927, issued to Brickell on Apr. 25, 2000; U.S. Pat. No. 5,869,619, issued to Studnicka on Feb. 9, 1999; U.S. Pat. No. 5,861,155, issued to Lin on Jan. 19, 1999; U.S. Pat. No. 5,712,120, issued to Rodriquez et al on Jan. 27, 1998; and U.S. Pat. No. 4,816,567, issued to Cabilly et al on Mar. 28, 1989, relevant portions incorporated herein by reference.

Humanized forms of antibodies are chimeric immunoglobulins, immunoglobulin chains or fragments thereof (such as Fab, Fab', F(ab')$_2$, Fv, scFv or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., 1986; Riechmann et al., 1988; Verhoeyen et al., 1988), by substituting nonhuman (i.e. rodent, chicken) CDRs or CDR sequences for the corresponding sequences of a human antibody. (See also U.S. Pat. No. 5,225,539.) In some instances, F, framework residues of the human immunoglobulin are replaced by corresponding non-human residues from the donor antibody. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin.

The aAb of the present invention can also include an engineered sequence or glycosylation sites that confer preferred levels of activity in antibody dependent cellular cytotoxicity (ADCC), antibody-dependent cellular phago-cytosis (ADCP), antibody-dependent neutrophil phagocyto-sis (ADNP), or antibody-dependent complement deposition (ADCD) functions as measured by bead-based or cell-based assays or in vivo studies in animal models.

The aAb can be a single chain variable fragment (scFv) that is a fusion of the variable regions of the heavy and light chains of immunoglobulins. This chimeric molecule retains the specificity of the original immunoglobulin, despite removal of the constant regions and the introduction of a linker peptide between the two antigen binding domains. This modification usually leaves the specificity unaltered after cleavage of the linker. These molecules were created historically to facilitate phage display where it is highly convenient to express the antigen-binding domain as a single peptide. The scFv can be created directly from subcloned heavy and light chains derived from a hybridoma or B cell. Single chain variable fragments lack the constant Fc region found in complete antibody molecules, and thus, the com-mon binding sites (e.g., protein A/G) used to purify anti-bodies. These fragments can often be purified/immobilized using Protein L since Protein L interacts with the variable region of kappa light chains.

The present invention includes activatable antibodies (also referred to as pro-antibodies, or probodies) that target specific antigens. Examples of antigens include first antigen is a tissue specific surface antigen selected from ICAM1; VCAM1; EpCAM; extra domain B of fibronectin; mela-noma-associated chondroitin sulfate proteoglycan (MCSP); melanoma-associated proteoglycan (MAPG); high molecu-lar weight melanoma associated antigen (HMV-MAA); prostate specific membrane antigen (PSMA); epidermal growth factor receptor (EGFR); hepatocyte growth factor receptor (HGFR); fibroblast activation protein (FAP); car-cinoembryonic antigen (CEA); cell-adhesion molecule (CAM); human B-cell maturation target (BCMA); placental growth factor (PLGF); folate receptor, insulin-like growth factor receptor (ILGFR); CD133; CD40; CD37; CD33; CD30; CD28; CD24; CD23; CD22; CD21; CD20; CD19; CD13; CD10; HER3; HER2; nonmuscle myosin heavy chain type A (nmMHCA); transferrin; epithelial cell adhe-sion molecule (EpCAM); annexin A 1; nucleotin, tenascin, vascular endothelial growth factor receptor 1 (VEGFR1), vascular endothelial growth factor receptor 2 (VEGFR-2); aminopeptidase N, tie-1, tie-2, or c-Met. Other antigens include a protein, a portion of a protein, or a peptides encoded by at least one gene selected from: ABCF1; ACVR1; ACVRIB; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1; B7.1; B7.2; BAD; BAFF; BAGI; BAII; BCL2; BCL6; BDNF; BLNK; BLR1 (MDR15); BlyS; BMP1; BMP2; BMP3B (GDF10); BMP4; BMP6; BMP8; BMPRIA; BMPRIB; BMPR2; BPAGI (plectin); BRCA1; C19orf10 (IL27w); C3; C4A; C5; C5R1; CANTI; CASPI; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-la); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-IRB/RA); CCR3 (CKR3/CMKBR3);

CCR4; CCR5 (CMKBR5/ChemR 13); CCR6 (CMKBR6/CKR-L3/STRL22/DRY6); CCR7 (CKR7/EBI1); CCR8 (CMKBR8/TER1/CKR-L1); CCR9 (GPR-9-6); CCRLI (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/Cipl); CDKNIB (p27Kipl); CDKNIC; CDKN2A (p16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (clau-din-7); CLN3; CXCLIO (IP-IO); CXCL11 (I-TAC/IP-9); CXCL12 (SDF1); CXCL13; CXCL14; CXCL16; CXCL2 (GR02); CXCL3 (GR03); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTRI; CGRP; Clq; Clr; CI; C4a; C4b; C2a; C2b; C3a; C3b; DAB2IP; DES; DKFZp451J0118; DNCLI; DPP4; E-selectin; E2F1; ECGF1; EDG1; EFNA1; EFNA3; EFNB2; EGF; EGFR; ELAC2; ENG; ENOI; EN02; EN03; EPHB4; EPO; ERBB2 (Her-2); EREG; ERK8; ESRI; ESR2; F3 (TF); Factor VII; Factor IX; Factor V; Factor Vila; Factor Factor X; Factor XII; Factor XIII; FADD; FasL; FASN; FCERIA; FCER2; Fc gamma receptor; FCGR3A; FGF; FGFI (aFGF); FGF10; FGF11; FGF12; FGF12B; FGF1 3; FGF1 4; FGF16; FGF1 7; FGF1 8; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FILI (EPSILON); FILI (ZETA); FLJ12584; FLJ25530; FLRTI (fibronectin); FLTI; FOS; FOSLI (FRA-1); FY (DARC); GABRP (GABAa); GAGEBI; GAGECI; GALNAC4S-6ST; GATA3; GDF5; GFII; GGTI; GMCSF; GNAS1; GNRH1; GPR2 (CCR10); GPR31; GPR44; GPR81 (FKSG80); GRCC10 (CIO); GRP; GSN (Gelsolin); GSTP1; glycoprotein (GP) Ilb/IIIa; HAVCR2; HDAC4; HDAC5; HDAC7A; HDAC9; Her2; HGF; ITGB4 (b 4 integrin); JAG1; JAK1; JAK3; JUN; K6HF; KAII; KDR; KITLG; KLF5 (GC Box BP); KLF6; KLK10; KLK12; KLK13; KLK14; KLK15; KLK3; KLK4; KLK5; KLK6; KLK9; KRTI; KRT19 (Keratin 19); KRT2A; KRTHB6 (hair-specific type II keratin); L-selectin; *LAMA5*; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB 1; midkine; MIF; MIP-2; MKI67 (Ki-67); MMP2; MMP9; MS4A1; MSMB; MT3 (metallothionectin-III); MTSSI; MUCI (mu-cin); MYC; MYD88; NCK2; neurocan; NKG2D; NFKB1; NFKB2; NGF; NGFB (NGF); NGFR; NgR-Lingo; NgR-Nogo66 (Nogo); NgR-p75; NgR-Troy; NME1 (NM23A); NOX5; NPPB; NROB1; NROB2; NRID1; NR1D2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRDI; P2RX7; PAP; PARTI; PATE; PAWR; PCA3; PCNA; PDGFA; PDGFB; PECAMI; PF4 (CXCL4); PGE2; PGF; PGR; phosphacan; PIAS2; PIK3CG; plasminogen activator; PLAU (uPA); PLG; PLXDC1; PPBP (CXCL7); PPID; PRI; PRKCQ; PRKDI; PRL; PROC; Protein C; PROK2; PSAP; PSCA; PTAFR; PTEN; PTGS2 (COX-2); PTN; RAC2 (p21Rac2); RAGE; RARB; RGSI; RGS13; RGS3; RNFIIO (ZNF144); ROB02; SI00A2; SCGB1D2 (lipophilin B); SCGB2A1 (mammaglobin 2); SCGB2A2 (mammaglobin 1); SCYEI (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRRIB (Sprl); ST6GAL1; STAB1; STAT6; STEAP; STEAP2; substance P; TB4R2; TBX21; TCP10; TDGF1; TEK; TGFA; TGFB1; TGFB111; TGFB2; TGFB3; TGFBI; TGFBR1; TGFBR2; TGFBR3; THIL; THBSI (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-α; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFS-FIO (TRAIL); TNFSF11 (TRANCE); TNFSF12 (AP03L); TNFSF13 (April); TNFSF13B; TNFSF14 (HVEML); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TREM1; TREM2; TRPC6; TSLP; TWEAK; thrombomodulin; thrombin; VEGF; VEGFB; VEGFC; versican; VHL C5; VLA-4; XCL1 (lymphotactin); XCL2 (SCM-1b); XCR1 (GPR5/CCXCR1); YY1; and/or ZFPM2.

The present invention also includes tumor targeting antigens selected from HER1, HER2, HER3, GD2, carcinoembryonic antigens (CEAs), epidermal growth factor receptor active mutant (EGFRVIII), CD133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUCI, prostate stem cell antigen (PSCA), Wilms tumor-1 (WT-1), or a Claudin family protein.

The present invention also includes antigen binding domains that target T-cell markers. Examples of T-cell marker include CTLA-4, PD-1, Lag3, S15, B7H3, B7H4, TCR-alpha, TCR-beta, and/or TIM-3. The antibodies may also bind to activating T cell markers, CD3, 41BB or OX40.

The present invention also includes cleavable linkers, such as protease cleavable linkers. Examples of cleavable linker are peptides that include sequences cleaved by a tumor associated protease: MMP1, MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B. Other examples include a cleavable linker that is cleaved by proteases upregulated during apoptosis or inflammation associated responses, e.g., a caspase. Examples of caspases are Caspase 1, Caspase 2, Caspase 3, Caspase 4, Caspase 5, Caspase 6, Caspase 7, Caspase 8, Caspase 9, Caspase 10, Caspase 11, and/or Caspase 12. Unlike the activatable antibodies of the prior art, the cleavable linker of the present invention does not directly mask an antigen binding site.

The present invention can also include a cytokine with the aAb, e.g., as part of the aAb fusion protein or attached separately to the aAb. The cytokine can be selected from at least one of: growth hormone; parathyroid hormone; thyroxine; insulin; proinsulin; relaxin; prorelaxin; glycoprotein hormones; hepatic growth factor; fibroblast growth factor; prolactin; placental lactogen; TNF-a; mullerian-inhibiting substance; gonadotropin-associated peptide; inhibin; activin; vascular endothelial growth factor; integrin; thrombopoietin (TPO); nerve growth factors; platelet-growth factor; placental growth factor, transforming growth factors (TGFs); insulin-like growth factor-1 and -11; erythropoietin (EPO); osteoinductive factors; interferons; colony stimulating factors (CSFs); lymphotoxin-alpha; lymphotoxin-beta; CD27L; CD30L; FASL; 4-1 BBL; OX40L; TRAIL; IL-1; IL-2; IL-3; IL-4; IL-5; IL-6; IL-7; IL-8; IL-9; IL-10; IL-11; IL-12; IL-13; IL-15; IL-18; IL-21; IL-22; IL-23; IL-33; IFN-a; IFN-b; IFN-g; IFN-g inducing factor (IGIF); bone morphogenetic protein (BMP); leukemia inhibitory factor (LIF); or kit ligand (KL).

The pro-antibody design of the present invention. To avoid the off-target Ag-Ab interaction, the strategy of the present invention is to reduce or even block the antigen binding of antibody via introducing a proteolytic linker to twist the protein structure of the antigen binding site. After the linker is cut at the target site, the two portions of the antibody that, together, form the antigen binding region of the antibody are released from the twisted structure and the antibody regains its antigen binding ability.

The design and method of the fusion protein disclosed herein can be applied to all kinds of antibody without adding extra-elements into the antibody structure. Further, it was found that the short linkers that reduce immunogenicity and high production of antibody. Further, the present invention includes no repeated G4S linkers, thereby reducing the problem with aggregation of the fusion protein prior to cleavage linker.

Example 1

Materials and Methods. Cloning and Protein Production

DNA fragments for protein expression were either synthesized by Genewiz or produced by PCR and cloned into pEE6.4 vector via isothermal assembly (Quantabio).

For protein expression, plasmids were mixed with PEI (Sigma) in 293 Free style medium (Gibco) and transfected into 293F cells. The cells were incubated at 37° C. with shaking at 120 rpm. After a 5~6 day incubation, the supernatant was harvested and filtered. The proteins were purified using Protein A resin (Repligen) and stored in neutralized elution buffer (40 mM Tris pH7.0/100 mM Glycine/100 mM NaCl).

ELISA and Cell-based ELISA. For testing the binding strength of anti-CTLA4 antibodies, CTLA4 proteins (Sino Biological) were diluted to 2 ug/ml and coated on the 96 well plate. Testing antibodies were diluted to different concentrations and added to the wells. After a 1-hour incubation at 37° C., the unbound protein was washed away with wash buffer (PBS/0.05% Tween 20). The detecting antibody (AP-Goat-anti-human IgG from Jackson ImmunoResearch) was added. After a 1-hour incubation at 37° C., the unbound protein was washed away with wash buffer. Then the PNPP substrate (Pierce) solution was added. Incubate at room temperature until yellow color develops. OD405 was measured using Biotek Epoch 2 and analyzed using Gen5 software. For testing the binding strength of anti-CLDN18.2 proteins, the method is as above except CLDN18.2 expressing KatoIII cells (ATCC) were coated on the 96 well plate instead of protein. Each well contained $10^5$ cells.

T-cell activation assay. For testing the ability to activate T cell for Pro-anti-CLDN18.2-Fc-CD3 before and after MMP14 cutting, Jurkat NFAT cells (InvivoGen), KatoIII cells (ATCC) and diluted proteins before and after MMP14 cutting were mixed in each well of 96-well plate. Each well contains 104 Jurkat cells and 104 KatoIII cells. After a 30-hour incubation at 37° C., 30 ul of supernatant was transferred from each well to a black 96 well plate.

QUANTI-Luc assay solution (InvivoGen) was then injected to measure luciferase activity using a luminometer (Biotek Synergy) and analyzed using Gen5 software.

```
Protein sequences
Pro-anti-CTLA4-Fc
                                        (SEQ ID NO: 1)
MINEFSSLAGAQRQRLLGVVVVQSLVHHGAAKHVALLPSALVHCQIASES

KAAVGIQHGHGGLVVVLGLAVAFPFHGDIARVEALHQTAQRHLILGQLVS

AGRLGVHLRLPRLAFGLADGLLNGGGQSLVGDLALVLLAVEPVLVQHGQH

GHHSICGVVLLLSGLGFGVVHFDAVHVPVKLHLGVLMADVHHHACHLGCS

RDHQCILGFGREQKHGRSAQQFGSRTARNRYHRALTPIVEVAGLTRTVIS

RGVLGGYRVNLQKELVFRGVTGDRDTRFDRRVVIGRTFIIDETHPFNFLT

WELTDPIPTITGGDGGAGNRARQAERTGRINQTRTRFFQFYLSAYVLTPP

FDFQLGARTERVRIVVPLLAVVKRLVFVLNRRNGQREVGTRARTTETVRN

AGVTGRRVVDQQFRRLTRLLHVPIQIVGFRVRVEQALRAFARDGRFFTRR

HAQRRWRLGHHNVSGGTWNPEQQYP

Pro-anti-CLDN18.2-Fc
                                        (SEQ ID NO: 2)
METDTLLLWVLLLWVPGSTGDIVMTQSPDSLAVSLGERATISCKSSQSLL

NSGNQKNYLTWYQQKPGQPPKLLIYWASTRESGVPDRFSGSGSGTDFTLT

ISSLQAEDVAVYYCQNDYFYPFTFGQGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGECGSSGRSENIR

TAGGSQVQLVQSGAEVKKPGSSVKVSCKASGYAFSNYLIEWVKQAPGQGL

EWIGLINPGSGGTNYNEKFKGKATITADKSTSTAYMELSSLRSEDTAVYY

CARVYYGNSFAYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGK

Pro-anti-CLDN18.2-Fc-CD3
                                        (SEQ ID NO: 3)
METDTLLLWVLLLWVPGSTGDIVMTQSPDSLAVSLGERATISCKSSQSLL

NSGNQKNYLTWYQQKPGQPPKLLIYWASTRESGVPDRFSGSGSGTDFTLT

ISSLQAEDVAVYYCQNDYFYPFTFGQGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGECGSSGRSENIR

TAGGSQVQLVQSGAEVKKPGSSVKVSCKASGYAFSNYLIEWVKQAPGQGL

EWIGLINPGSGGTNYNEKFKGKATITADKSTSTAYMELSSLRSEDTAVYY

CARVYYGNSFAYWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPEAAGGPSVFLFP
```

```
                    -continued

PKPKDTLMISRTPEVTCVVVDVSHEDPEVKFNWYVDGVEVHNAKTKPREE

QYNSTYRVVSVLTVLHQDWLNGKEYKCKVSNKALGAPIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGKGGGGSGGGGSGGGGSGGGGSQIVLTQSPAIMSASPGEKVTMTCSASS

SVSYMNWYQQKSGTSPKRWIYDTSKLASGVPAHFRGSGSGTSYSLTISGM

EAEDAATYYCQQWSSNPFTFGSGTKLEINGGGGSGGGGSGGGGSQVQLQQ

SGAELARPGASVKMSCKASGYTFTRYTMHWVKQRPGQGLEWIGYINPSRG

YTNYNQKFKDKATLTTDKSSSTAYMQLSSLTSEDSAVYYCARYYDDHYCL

DYWGQGTTLTVSS
```

Figure 1B:
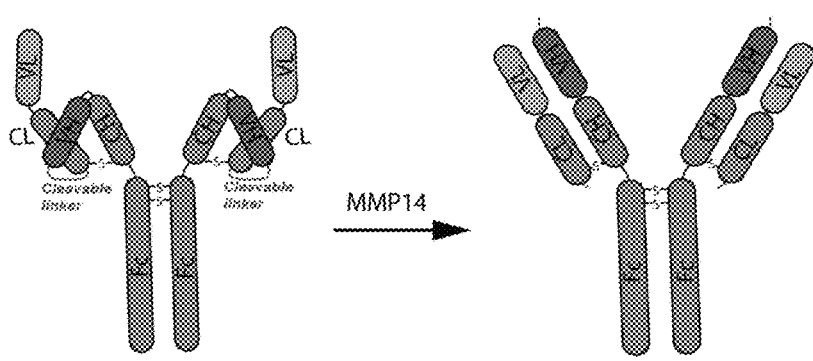
Figure 1C:
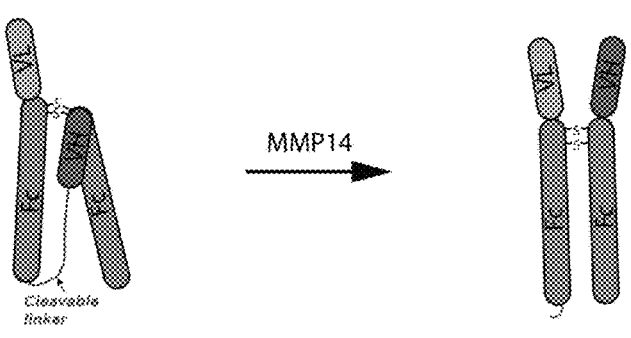

FIGS. 1A-1C show schematic diagrams of proteins and diagrams to show how Pro antibody designs regains the antigen binding ability after cutting. FIG. 1A. The schematics of AABs. FIG. 1B shows the first type of antigen binding activation. CL and VH is linked with a proteolytic linker sensitive to MMP14. VH is not able to pair with VL to form a stable antigen binding site before cutting. VH is released after cutting with MMP14 and is able to pair with VL to form the antigen binding site. FIG. 1C shows the second type of antigen binding activation. The first Fc and VH is linked with a proteolytic linker sensitive to MMP14. VH is not able to pair with VL to form a stable antigen binding site before cutting. VH is released after cutting with MMP14 and is able to pair with VL to form the antigen binding site.

Figure 2:
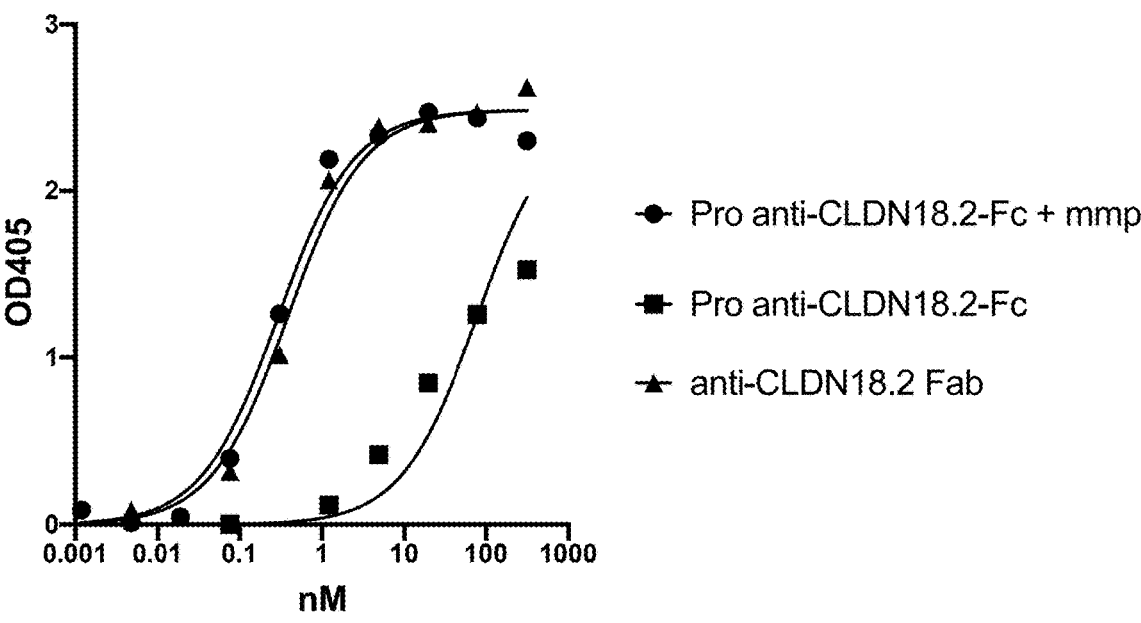
FIG. 2: Pro anti-CLDN18.2-Fc restores the antigen binding ability after the linker is cut with MMP14. Cell-based ELISA data shows that pro anti-CLDN18.2-Fc after cutting with MMP14 binds to the CLDN18.2 expressing KatoIII cells as strong as the positive control. The binding of uncut protein is about 100 times weaker to the positive control.

FIG. 2 is a graph that shows a Pro anti-CLDN18.2-Fc restores the antigen binding ability after the linker is cut with MMP14. Cell-based ELISA data shows that pro anti-CLDN18.2-Fc after cutting with MMP14 binds to the CLDN18.2 expressing KatoIII cells as strong as the positive control. The binding of uncut protein is about 100 times weaker to the positive control.

Figure 3:
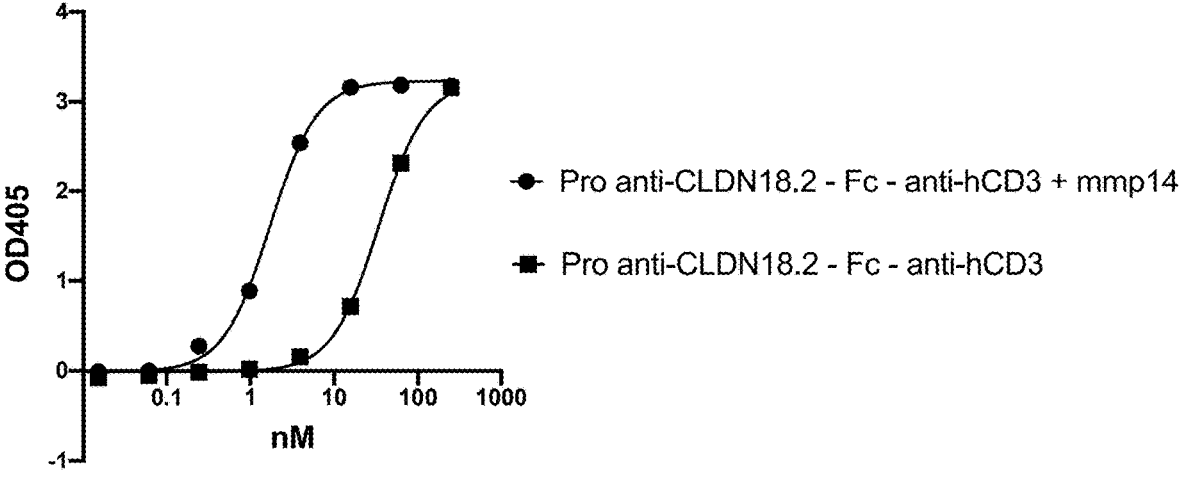
FIG. 3: Bi-specific pro anti-CLDN18.2-Fc-anti-hCD3 restores the antigen binding ability after the linker is cut with MMP14. Cell-based ELISA data shows that pro anti-CLDN18.2-Fc-anti-hCD3 after cutting with MMP14 binds to the CLDN18.2 expressing KatoIII cells more than 20 times stronger than that of uncut proteins.

FIG. 3 is a graph that shows a Bi-specific pro anti-CLDN18.2-Fc-anti-hCD3 restores the antigen binding ability after the linker is cut with MMP14. Cell-based ELISA data shows that pro anti-CLDN18.2-Fc-anti-hCD3 after cutting with MMP14 binds to the CLDN18.2 expressing KatoIII cells more than 20 times stronger than that of uncut proteins.

Figure 4:
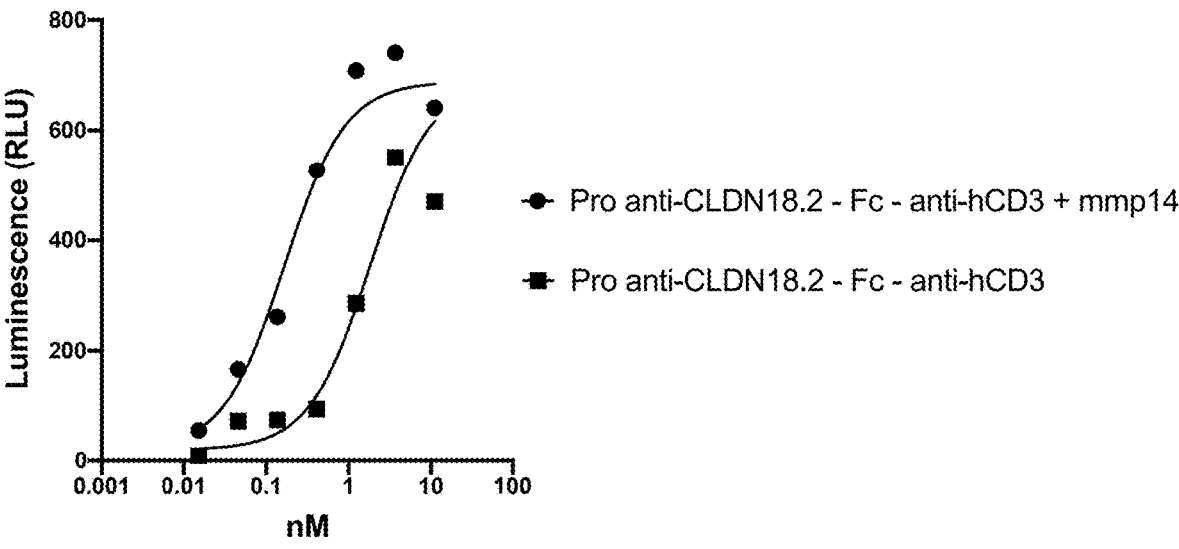
FIG. 4: Bi-specific pro anti-CLDN18.2-Fc-anti-hCD3 after MMP14 cutting activates T cells more than 10 times stronger than that of uncut protein. Reporter Jurkat cells were mixed with KatoIII cells and pro anti-CLDN18.2-Fcanti-hCD3 with or without MMP14 cutting. After 24 hours incubation, the level of T cell activation was measured via the luciferase production.

FIG. 4 is a graph that shows a Bi-specific pro anti-CLDN18.2-Fc-anti-hCD3 after MMP14 cutting activates T cells more than 10 times stronger than that of uncut protein. Reporter Jurkat cells were mixed with KatoIII cells and pro anti-CLDN18.2-Fc-anti-hCD3 with or without MMP14 cutting. After 24 hours incubation, the level of T cell activation was measured via the luciferase production.

Figure 5:
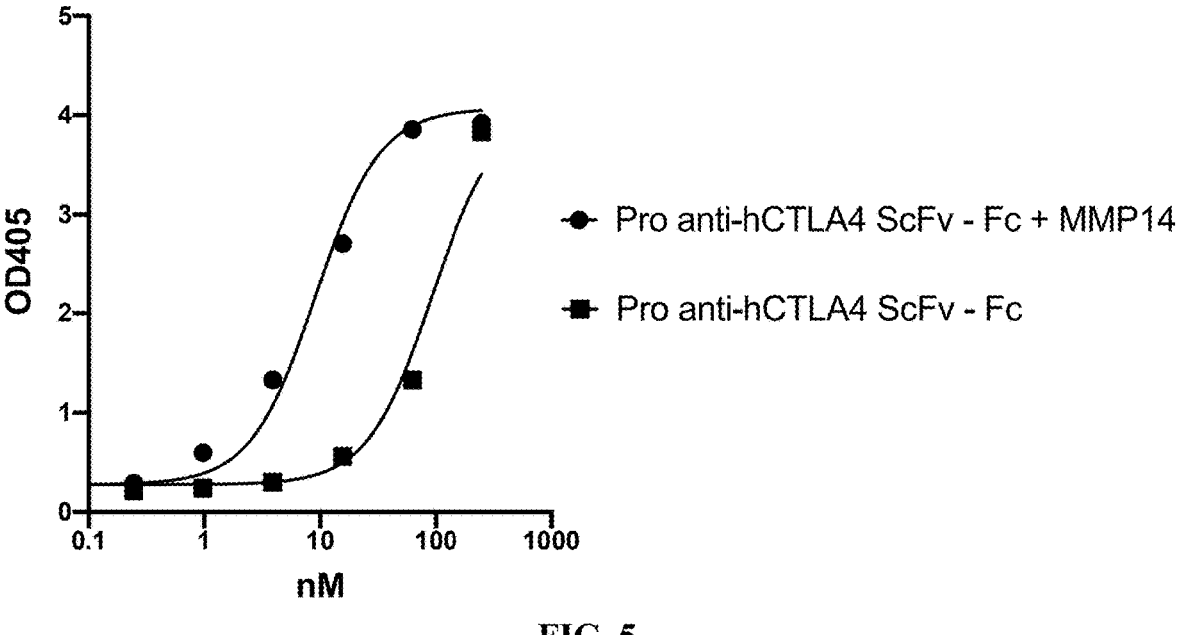
FIG. 5: Pro anti-hCTLA4 ScFv-Fc after cutting with MMP14 binds to surface coated hCTLA4 proteins more than 10 times stronger than uncut protein.

FIG. 5 is a graph that shows a Pro anti-hCTLA4 ScFv-Fc after cutting with MMP14 binds to surface coated hCTLA4 proteins more than 10 times stronger than uncut protein.

Figure 6:
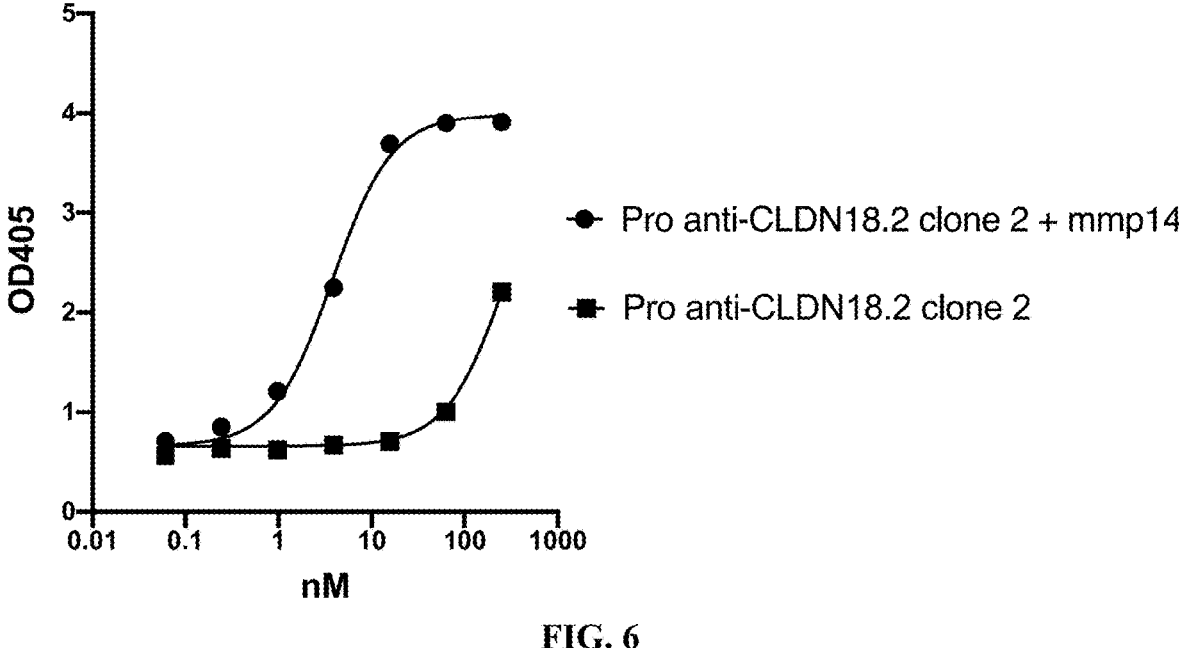
FIG. 6: Pro anti-CLDN18.2 clone 2 restores the antigen binding ability after the linker is cut with MMP14. Cell-based ELISA data shows that pro anti-CLDN18.2 clone 2 after cutting with MMP14 binds to the CLDN18.2 expressing KatoIII about 100× stronger than that of uncut protein.

FIG. 6 is a graph that shows a Pro anti-CLDN18.2 clone 2 restores the antigen binding ability after the linker is cut with MMP14. Cell-based ELISA data shows that pro anti-CLDN18.2 clone 2 after cutting with MMP14 binds to the CLDN18.2 expressing KatoIII about 100× stronger than that of uncut protein.

Figure 7:
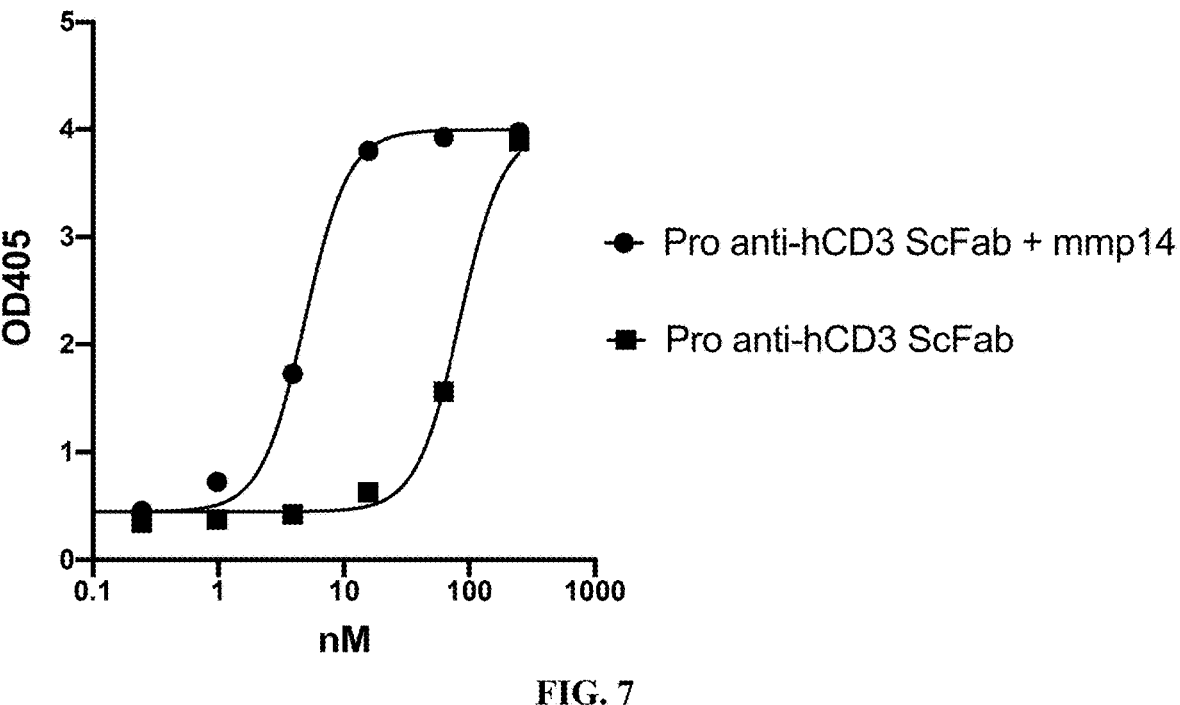
FIG. 7: Pro anti-hCD3 ScFab restores the hCD3e binding ability after the linker is cut with MMP14. ELISA data shows that pro anti-hCD3 ScFab after cutting with MMP14 binds to surface coated hCD3e more than 20× stronger than that of uncut protein.

FIG. 7 is a graph that shows a Pro anti-hCD3 ScFab restores the hCD3e binding ability after the linker is cut with MMP14. ELISA data shows that pro anti-hCD3 ScFab after cutting with MMP14 binds to surface coated hCD3e more than 20× stronger than that of uncut protein.

Figure 8:
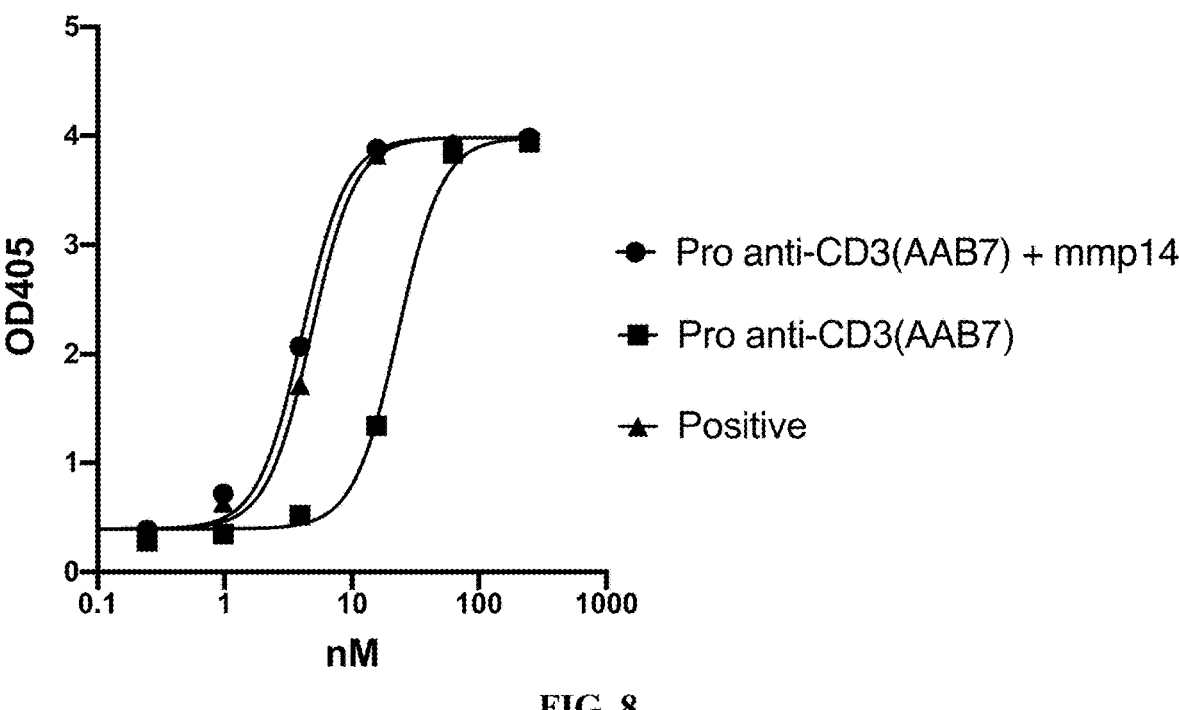
FIG. 8: Pro anti-hCD3 (AAB7) restores the hCD3e binding ability after the linker is cut with MMP14. ELISA data shows that pro anti-hCD3 (AAB7) after cutting with MMP14 binds to coated hCD3e more than 10× stronger than that of uncut protein.

FIG. 8 is a graph that shows a Pro anti-hCD3 (AAB7) restores the hCD3e binding ability after the linker is cut with MMP14. ELISA data shows that pro anti-hCD3 (AAB7) after cutting with MMP14 binds to coated hCD3e more than 10× stronger than that of uncut protein.

Figure 9:
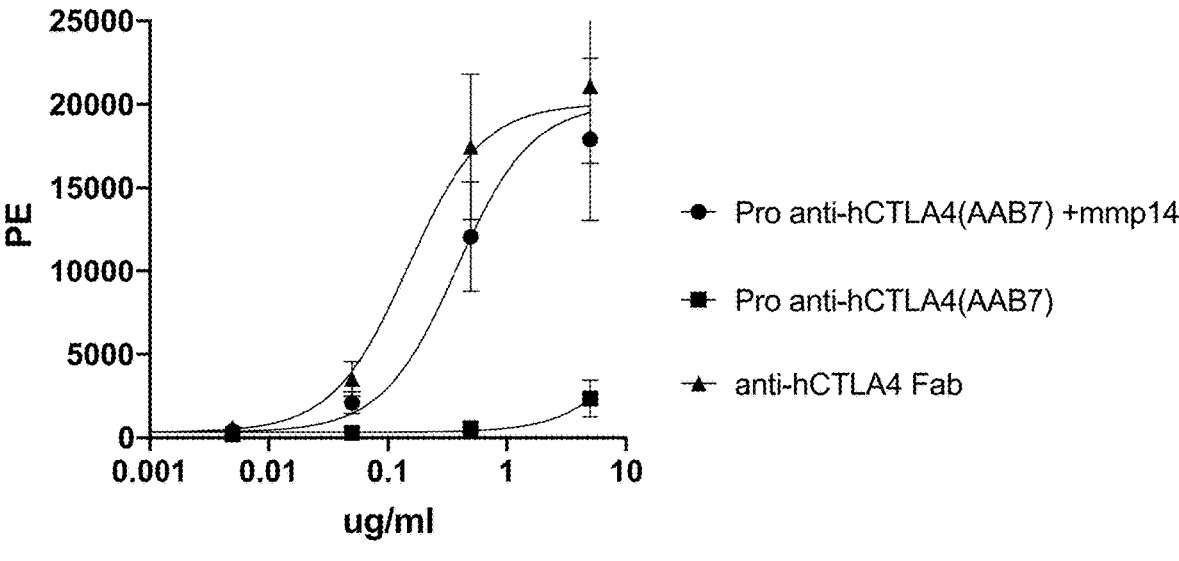
FIG. 9: Pro anti-hCTLA4 (AAB7) restores the antigen binding ability after the linker is cut with MMP14. Flow Cytometry-Based Binding Assay data shows that pro anti-hCTLA4 (AAB7) after cutting with MMP14 binds to the hCTLA4 expressing cells as strong as the positive control while the uncut protein shows almost no binding.

FIG. 9 is a graph that shows a Pro anti-hCTLA4 (AAB7) restores the antigen binding ability after the linker is cut with MMP14. Flow Cytometry-Based Binding Assay data shows that pro anti-hCTLA4 (AAB7) after cutting with MMP14 binds to the hCTLA4 expressing cells as strong as the positive control while the uncut protein shows almost no binding.

Figure 10:
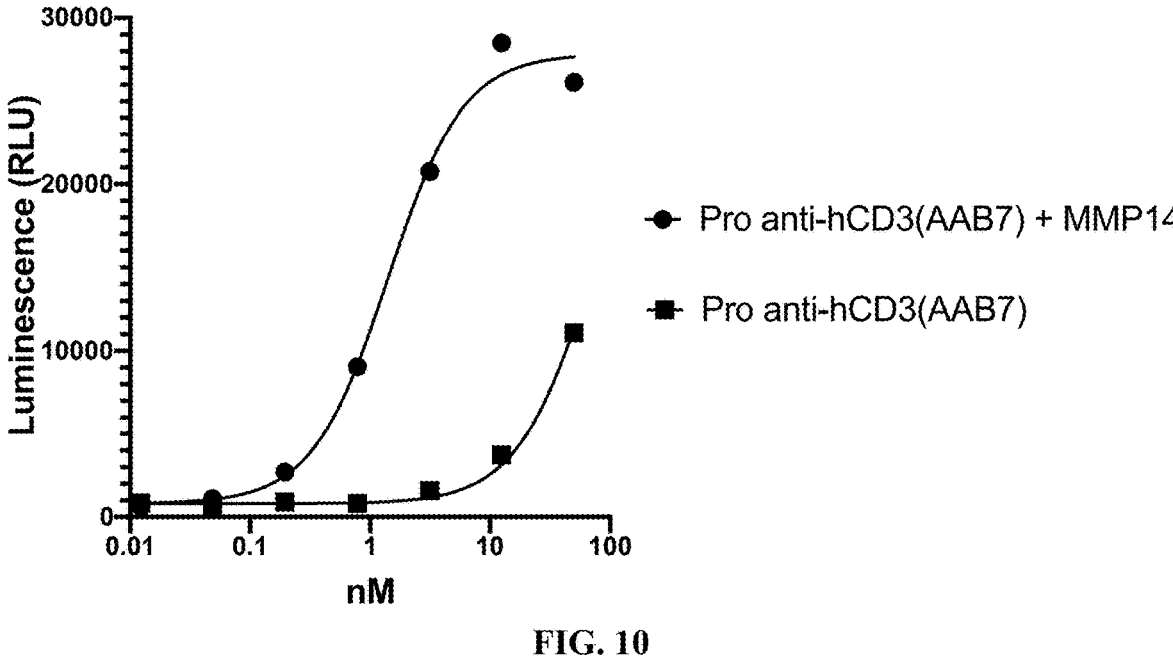
FIG. 10: Pro anti-hCD3 (AAB7) restores the ability to stimulate T cell activation after the linker is cut with MMP14. Reporter T cell activation assay data shows that pro anti-hCD3 (AAB7) after cutting with MMP14 stimulates T cell activation more than 20× stronger than that of uncut protein. The level of T cell activation is measured via the luciferase production.

FIG. 10 is a graph that shows a Pro anti-hCD3 (AAB7) restores the ability to stimulate T cell activation after the linker is cut with MMP14. Reporter T cell activation assay data shows that pro anti-hCD3 (AAB7) after cutting with MMP14 stimulates T cell activation more than 20× stronger than that of uncut protein. The level of T cell activation is measured via the luciferase production.

Figure 11:
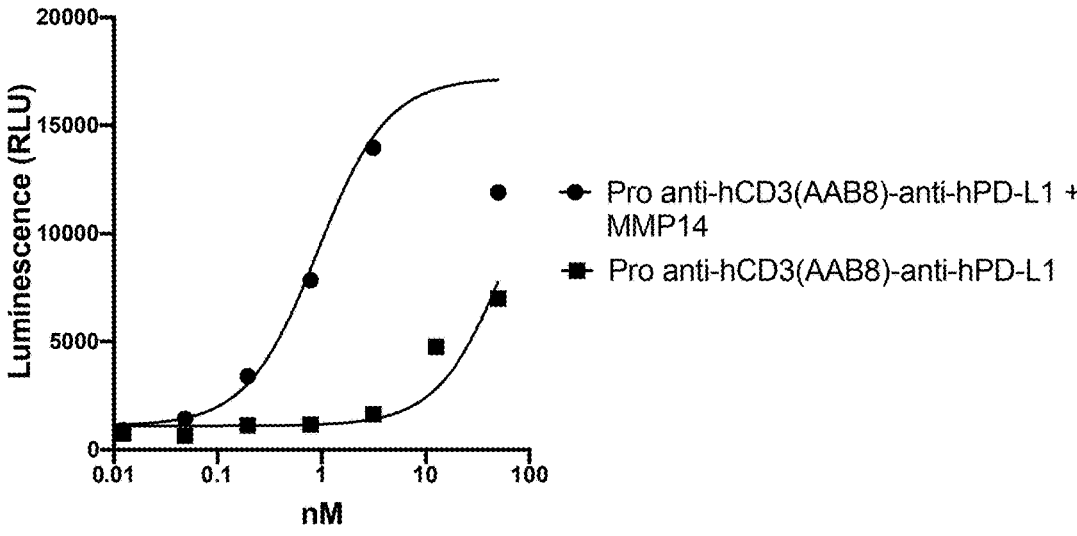
FIG. 11: Bi-specific Pro anti-hCD3 (AAB8)-anti-hPD-L1 restores the ability to stimulate T cell activation after the linker is cut with MMP14. Reporter T cell activation assay data shows that Bi-specific Pro anti-hCD3 (AAB8)-anti-hPD-L1 after cutting with MMP14 stimulates T cell activation more than 20× stronger than that of uncut protein. The level of T cell activation is measured via the luciferase production.

FIG. 11 is a graph that shows a Bi-specific Pro anti-hCD3 (AAB8)-anti-hPD-L1 restores the ability to stimulate T cell activation after the linker is cut with MMP14. Reporter T cell activation assay data shows that Bi-specific Pro anti-hCD3 (AAB8)-anti-hPD-L1 after cutting with MMP14 stimulates T cell activation more than 20× stronger than that of uncut protein. The level of T cell activation is measured via the luciferase production.

Figure 12:
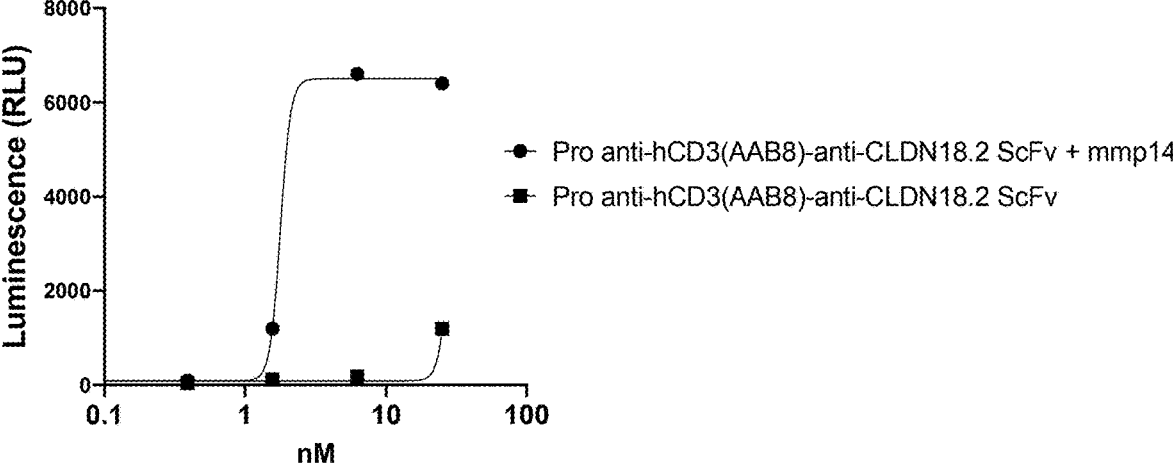
FIG. 12: Bi-specific Pro anti-hCD3 (AAB8)-anti-CLDN18.2 ScFv restores the ability to stimulate T cell activation after the linker is cut with MMP14. Reporter T cell activation assay data shows that Bi-specific Pro anti-hCD3 (AAB8)-anti-CLDN18.2 ScFv after cutting with MMP14 stimulates T cell activation more than 20× stronger than that of uncut protein. The level of T cell activation is measured via the luciferase production.

FIG. 12 is a graph that shows a Bi-specific Pro anti-hCD3 (AAB8)-anti-CLDN18.2 ScFv restores the ability to stimulate T cell activation after the linker is cut with MMP14. Reporter T cell activation assay data shows that Bi-specific Pro anti-hCD3 (AAB8)-anti-CLDN18.2 ScFv after cutting with MMP14 stimulates T cell activation more than 20× stronger than that of uncut protein. The level of T cell activation is measured via the luciferase production.

Figure 13:
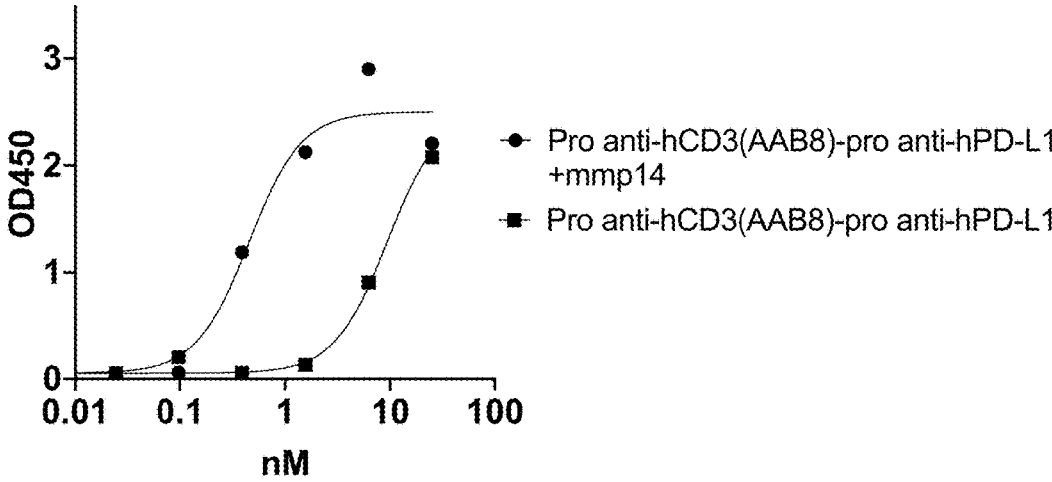
FIG. 13: Bi-specific Pro anti-hCD3 (AAB8)-pro anti-hPD-L1 restores the ability to stimulate T cell activation in PBMC after the linker is cut with MMP14. Bi-specific Pro anti-hCD3 (AAB8)-pro anti-hPD-L1 after cutting with MMP14 stimulates T cell activation in PBMC more than 20× stronger than that of uncut protein. The level of T cell activation is measured via the IFN-gamma production.

FIG. 13 is a graph that shows a Bi-specific Pro anti-hCD3 (AAB8)-pro anti-hPD-L1 restores the ability to stimulate T cell activation in PBMC after the linker is cut with MMP14. Bi-specific Pro anti-hCD3 (AAB8)-pro anti-hPD-L1 after cutting with MMP14 stimulates T cell activation in PBMC more than 20× stronger than that of uncut protein. The level of T cell activation is measured via the IFN-gamma production.

Figure 14:
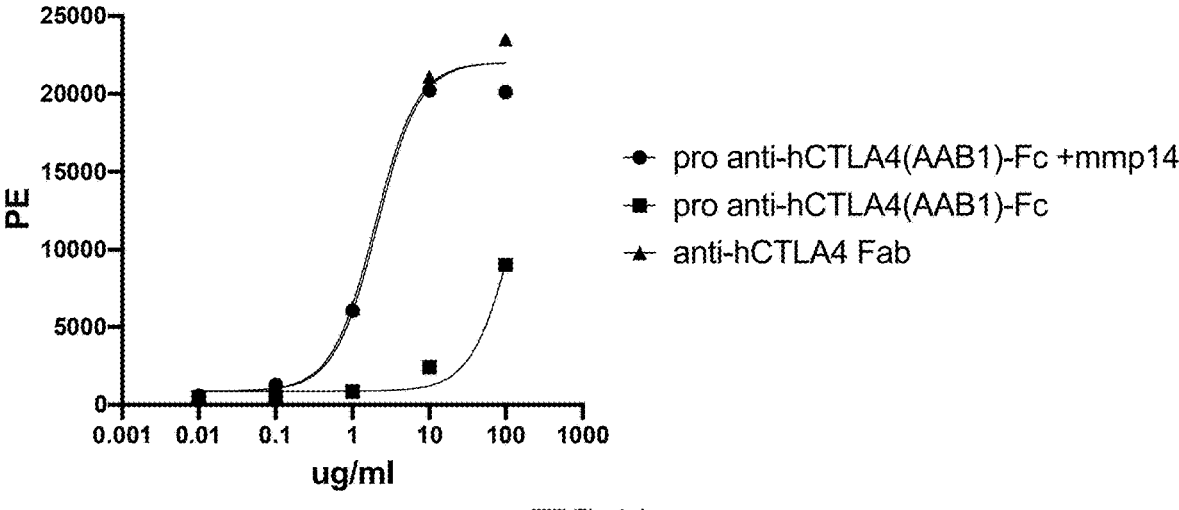
FIG. 14: Pro anti-hCTLA4 (AAB1)-Fc restores the antigen binding ability after the linker is cut with MMP14. Flow Cytometry-Based Binding Assay data shows that pro anti-hCTLA4 (AAB1)-Fc after cutting with MMP14 binds to the hCTLA4 expressing cells as strong as the positive control while the uncut protein shows almost no binding.

FIG. 14 is a graph that shows a Pro anti-hCTLA4 (AAB1)-Fc restores the antigen binding ability after the linker is cut with MMP14. Flow Cytometry-Based Binding Assay data shows that pro anti-hCTLA4 (AAB1)-Fc after cutting with MMP14 binds to the hCTLA4 expressing cells as strong as the positive control while the uncut protein shows almost no binding.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property (ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least +1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

---

What is claimed is:

1. An activatable antibody (aAb) comprising, in order, the following structure:

a first light chain comprising:

a first variable light region and constant light region;

a first heavy chain consisting of:

a first variable heavy region, a constant heavy region, and an Fc region; and a cleavable linker between the constant light region and the first variable heavy region, wherein the cleavable linker prevents or reduces the first variable heavy region from pairing with the first variable light region to form a first antigen binding site against a first antigen; and wherein cleavage of the cleavable linker releases the first variable heavy region to pair with the first variable light region to form the first antigen binding site to bind a first antigen.

2. The aAb of claim 1, wherein the aAb further comprises a second antigen binding site formed by a second variable light chain and a second variable heavy chain connected to the first heavy chain that binds a second antigen, and optionally a flexible non-cleavable linker between the second variable light chain and the second variable heavy chain.

3. The aAb of claim 1, wherein the first light chain, the first heavy chain, or both, further comprise an Fc region, a wild-type Fc region, a mutated Fc region, a monomeric wild type Fc region, a monomeric mutant Fc region, a dimeric wild type Fc region, or a dimeric mutant Fc region, a second variable heavy region and a second Fc region, or a second variable heavy region and a second Fc region and an uncleavable flexible linker and a second variable light region and a second heavy variable region, or a second Fc region and an uncleavable flexible linker and a cytokine.

4. The aAb of claim 2, wherein the first and second antigen are at least one of:

the same antigen; the first and second antigen are different; or the first and second antigen is the same antigen but the first antigen binding site and the second antigen binding site bind different epitopes of the same antigen;

the first antigen binding site or the second antigen binding site binds a tumor target;

the first antigen is a tissue specific surface antigen selected from ICAM1; VCAM1; EpCAM; extra domain B of fibronectin; melanoma-associated chondroitin sulfate proteoglycan (MCSP); melanoma-associated proteoglycan (MAPG); high molecular weight melanoma associated antigen (HMV-MAA); prostate specific membrane antigen (PSMA); epidermal growth factor receptor (EGFR); hepatocyte growth factor receptor (HGFR); fibroblast activation protein (FAP); carcinoembryonic antigen (CEA); cell-adhesion molecule (CAM); human B-cell maturation target (BCMA); placental growth factor (PLGF); folate receptor, insulin-like growth factor receptor (ILGFR); CD133; CD40; CD37; CD33; CD30; CD28; CD24; CD23; CD22; CD21; CD20; CD19; CD13; CD10; HER3; HER2; nonmuscle myosin heavy chain type A (nmMHCA); transferrin; epithelial cell adhesion molecule (EpCAM); annexin A 1; nucleotin, tenascin, vascular endothelial growth factor receptor 1 (VEGFR1), vascular endothelial growth factor receptor 2; (VEGFR-2); aminopeptidase N, tie-1, tie-2, or c-Met;

the first antigen is selected from a protein, a portion of a protein, or a peptides encoded by at least one gene selected from: ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1; B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orfl0 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-la); CCL4 (MIP-lb); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-IRB/RA); CCR3 (CKR3/CMKBR3); CCR4; CCR5 (CMKBR5/ChemR 13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74;

CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wapl/Cipl); CDKNIB (p27Kipl); CDKNIC; CDKN2A (pl6INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CXCLIO (IP-IO); CXCL11 (I-TAC/IP-9); CXCL12 (SDF1); CXCL13; CXCL14; CXCL16; CXCL2 (GR02); CXCL3 (GR03); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; CGRP; Clq; Clr; Cl; C4a; C4b; C2a; C2b; C3a; C3b; DAB2IP; DES; DKFZp451J0118; DNCL1; DPP4; E-selectin; E2F1; ECGF1; EDG1; EFNA1; EFNA3; EFNB2; EGF; EGFR; ELAC2; ENG; ENOI; EN02; EN03; EPHB4; EPO; ERBB2 (Her-2); EREG; ERK8; ESR1; ESR2; F3 (TF); Factor VII; Factor IX; Factor V; Factor Vila; Factor X; Factor XII; Factor XIII; FADD; FasL; FASN; FCER1A; FCER2; Fc gamma receptor; FCGR3A; FGF; FGFI (aFGF); FGF10; FGFII; FGF12; FGF12B; FGFI 3; FGFI 4; FGF16; FGFI 7; FGFI 8; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRTI (fibronectin); FLTI; FOS; FOSLI (FRA-1); FY (DARC); GABRP (GABAa); GAGEBI; GAGECI; GALNAC4S-6ST; GATA3; GDF5; GFII; GGTI; GMCSF; GNAS1; GNRH1; GPR2 (CCR10); GPR31; GPR44; GPR81 (FKSG80); GRCC10 (CIO); GRP; GSN (Gelsolin); GSTP1; glycoprotein (GP) Ilb/Illa; HAVCR2; HDAC4; HDAC5; HDAC7A; HDAC9; Her2; HGF; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); L-selectin; *LAMA*5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB 1; midkine; MIF; MIP-2; MKI67 (Ki-67); MMP2; MMP9; MS4A1; MSMB; MT3 (metallothionectin-III); MTSSI; MUCI (mucin); MYC; MYD88; NCK2; neurocan; NKG2D; NFKB1; NFKB2; NGF; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PARTI; PATE; PAWR; PCA3; PCNA; PDGFA; PDGFB; PECAM1; PF4 (CXCL4); PGE2; PGF; PGR; phosphacan; PIAS2; PIK3CG; plasminogen activator; PLAU (uPA); PLG; PLXDC1; PPBP (CXCL7); PPID; PR1; PRKCQ; PRKDI; PRL; PROC; Protein C; PROK2; PSAP; PSCA; PTAFR; PTEN; PTGS2 (COX-2); PTN; RAC2 (p21Rac2); RAGE; RARB; RGSI; RGS13; RGS3; RNFIIO (ZNF144); ROB02; SI00A2; SCGB1D2 (lipophilin B); SCGB2A1 (mammaglobin 2); SCGB2A2

(mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Sprl); ST6GAL1; STAB1; STAT6; STEAP; STEAP2; substance P; TB4R2; TBX21; TCP10; TDGF1; TEK; TGFA; TGFB1; TGFB111; TGFB2; TGFB3; TGFBI; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-α; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSFIO (TRAIL); TNFSF11 (TRANCE); TNFSF12 (AP03L); TNFSF13 (April); TNFSF13B; TNFSF14 (HVEML); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TREM1; TREM2; TRPC6; TSLP; TWEAK; thrombomodulin; thrombin; VEGF; VEGFB; VEGFC; versican; VHL C5; VLA-4; XCL1 (lymphotactin); XCL2 (SCM-lb); XCR1 (GPR5/CCXCR1); YY1; and ZFPM2;

the first antigen binding site or the second antigen binding site binds a T-cell activator;

the T-cell activator is selected from CD3, 41BB or OX40;

the tumor target is selected from a tumor targeting antigen, HER1, HER2, HER3, GD2, carcinoembryonic antigens (CEAs), epidermal growth factor receptor active mutant (EGFRVIII), CD133, Fibroblast Activation Protein Alpha (FAP), Epithelial cell adhesion molecular (Epcam), Glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUC1, prostate stem cell antigen (PSCA), Wilms tumor-1 (WT-1), or a Claudin family protein;

the first antigen binding site or the second antigen binding site binds a T-cell marker; or the T-cell marker is selected from CTLA-4, PD-1, Lag3, S15, B7H3, B7H4, TCR-alpha, TCR-beta, or TIM-3.

5. The aAb of claim 1, wherein the cleavable linker is a protease cleavable linker.

6. The aAb of claim 5, wherein the cleavable linker is cleaved by a tumor associated protease: MMP1, MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B; or the cleavable linker is cleaved by proteases upregulated during apoptosis or inflammation associated responses; or the cleavable linker is cleaved by a caspase;

wherein the caspase is Caspase 1, Caspase 2, Caspase 3, Caspase 4, Caspase 5, Caspase 6, Caspase 7, Caspase 8, Caspase 9, Caspase 10, Caspase 11 or Caspase 12.

7. The aAb of claim 1, wherein the cleavable linker does not mask an antigen binding site.

8. The aAb of claim 1, further comprising:

an agent conjugated to the aAb; or a cytokine attached to, or in a fusion protein with the aAb or an Fc region;

wherein the cytokine is selected from at least one of: growth hormone; parathyroid hormone; thyroxine; insulin; proinsulin; relaxin; prorelaxin; glycoprotein hormones; hepatic growth factor; fibroblast growth factor; prolactin; placental lactogen; TNF-α; mullerian-inhibiting substance; gonadotropin-associated peptide; inhibin; activin; vascular endothelial growth factor; integrin; thrombopoietin (TPO); nerve growth factors; platelet-growth factor; placental growth factor, transforming growth factors (TGFs); insulin-like growth factor-1 and-11; erythropoietin (EPO); osteoinductive factors; interferons; colony stimulating factors (CSFs); lymphotoxin-alpha; lymphotoxin-beta; CD27L; CD30L; FASL; 4-1 BBL; OX40L; TRAIL; IL-1; IL-2; IL-3; IL-4; IL-5; IL-6; IL-7; IL-8; IL-9; IL-10; IL-11; IL-12; IL-13; IL-15; IL-18; IL-21; IL-22; IL-23; IL-33; IFN-a; IFN-b; IFN-g; IFN-g inducing factor (IGIF); bone morphogenetic protein (BMP); leukemia inhibitory factor (LIF); or kit ligand (KL).

9. The aAb of claim 1, wherein the aAb comprises an amino acid sequence selected from SEQ ID NOS: 1, 2, or 3.

10. The aAb of claim 8, wherein the agent is at least one of: a toxin or toxic fragment thereof; a microtubule inhibitor; a nucleic acid damaging agent; a detectable moiety; or a diagnostic agent.

11. The aAb of claim 1, further comprising a pharmaceutically acceptable diluent or carrier.

12. An activatable antibody (aAb) comprising, in order, the following structure:

a first light chain comprising a first variable light region and a constant light region;

a cleavable linker; and a first heavy chain comprising a first variable heavy region and a constant heavy region;

wherein the cleavable linker prevents or reduces the first variable heavy region from pairing with the first variable light region to form a first antigen binding site against a first antigen; and wherein cleavage of the cleavable linker releases the first variable heavy region to pair with the first variable light region to form the first antigen binding site to bind a first antigen.

13. The aAb of claim 12, further comprising at least one of:

a first constant light region or a first constant heavy region, respectively; or an Fc region attached to a first constant heavy region, wherein the Fc region is a wild-type or a mutant domain that modifies Fc receptor binding.

14. The aAb of claim 12, wherein the aAb further comprises a second antigen binding site formed by a second variable light chain and a second variable heavy chain connected to the first heavy chain that binds a second antigen, and optionally a flexible non-cleavable linker between the second variable light chain and the second variable heavy chain;

further comprises an Fc region that is a wild-type Fc region, a mutated Fc region, a monomeric wild type Fc region, a monomeric mutant Fc region, a dimeric wild type Fc region, or a dimeric mutant Fc region, a second variable heavy region and a second Fc region, or a second variable heavy region and a second Fc region and an uncleavable flexible linker and a second variable light region and a second heavy variable region, or a second Fc region and an uncleavable flexible linker and a cytokine;

further comprising a cytokine attached to, or in a fusion protein with the aAb or the Fc region, and wherein the cytokine is selected from at least one of: growth hormone; parathyroid hormone; thyroxine; insulin; proinsulin; relaxin; prorelaxin; glycoprotein hormones; hepatic growth factor; fibroblast growth factor; prolactin; placental lactogen; TNF-alpha; mullerian-inhibiting substance; gonadotropin-associated peptide; inhibin; activin; vascular endothelial growth factor; integrin; thrombopoietin (TPO); nerve growth factors; platelet-growth factor; placental growth factor, transforming growth factors (TGFs); insulin-like growth factor-1 and-11; erythropoietin (EPO); osteoinductive factors; interferons; colony stimulating factors (CSFs); lymphotoxin-alpha; lymphotoxin-beta; CD27L; CD30L; FASL; 4-1 BBL; OX40L; TRAIL; IL-1; IL-2; IL-3; IL-4; IL-5; IL-6; IL-7; IL-8; IL-9; IL-10; IL-11; IL-12; IL-13; IL-15; IL-18; IL-21; IL-22; IL-23; IL-33; IFN-a; IFN-beta; IFN-gamma; IFN-gamma inducing factor (IGIF); bone morphogenetic protein (BMP); leukemia inhibitory factor (LIF); or kit ligand (KL).

15. The aAb of claim 12, wherein the first antigen is a tissue specific surface antigen selected from ICAM1; VCAM1; EpCAM; extra domain B of fibronectin; melanoma-associated chondroitin sulfate proteoglycan (MCSP); melanoma-associated proteoglycan (MAPG); high molecular weight melanoma associated antigen (HMV-MAA); prostate specific membrane antigen (PSMA); epidermal growth factor receptor (EGFR); hepatocyte growth factor receptor (HGFR); fibroblast activation protein (FAP); carcinoembryonic antigen (CEA); cell-adhesion molecule (CAM); human B-cell maturation target (BCMA); placental growth factor (PLGF); folate receptor, insulin-like growth factor receptor (ILGFR); CD133; CD40; CD37; CD33; CD30; CD28; CD24; CD23; CD22; CD21; CD20; CD19; CD13; CD10; HER3; HER2; nonmuscle myosin heavy chain type A (nmMHCA); transferrin; epithelial cell adhesion molecule (EpCAM); annexin A 1; nucleotin, tenascin, vascular endothelial growth factor receptor 1 (VEGFR1), vascular endothelial growth factor receptor 2; (VEGFR-2); aminopeptidase N, tie-1, tie-2, or c-Met; or the first antigen is selected from a protein, a portion of a protein, or a peptides encoded by at least one gene selected from: ABCF1; ACVR1; ACVR1B; ACVR2; ACVR2B; ACVRL1; ADORA2A; aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orfl0 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-la); CCL4 (MIP-Ib); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19;

CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wapl/Cipl); CDKNIB (p27Kipl); CDKNIC; CDKN2A (pl6INK4a); CDKN2B; CDKN2C; CDKN3; CEBPB; CER1; CHGA; CHGB; chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CXCLIO (IP-IO); CXCL11 (I-TAC/IP-9); CXCL12 (SDF1); CXCL13; CXCL14; CXCL16; CXCL2 (GR02); CXCL3 (GR03); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; CGRP; Clq; CIR protein; CI; C4a; C4b; C2a; C2b; C3a; C3b; DAB2IP; DES; DKFZp451J0118; DNCL1; DPP4; E-selectin; E2F1; ECGF1; EDG1; EFNA1; EFNA3; EFNB2; EGF; EGFR; ELAC2; ENG; ENOI; EN02; EN03; EPHB4; EPO; ERBB2 (Her-2); EREG; ERK8; ESR1; ESR2; F3 (TF); Factor VII; Factor IX; Factor V; Factor VIIa; Factor X; Factor XII; Factor XIII; FADD; FasL; FASN; FCER1A; FCER2; Fc gamma receptor; FCGR3A; FGF; FGFI (aFGF); FGF10; FGFII; FGF12; FGF12B; FGFI 3; FGFI 4; FGF16; Fgfl7; Fgfl 8; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FUJ12584; FLJ25530; FLRTI (fibronectin); FLTI; FOS; FOSLI (FRA-1); FY (DARC); GABRP (GABAa); GAGEBI; GAGECI; GALNAC4S-6ST; GATA3; GDF5; GFII; GGTI; GMCSF; GNAS1; GNRH1; GPR2 (CCR10); GPR31; GPR44; GPR81 (FKSG80); GRCC10 (CIO); GRP; GSN (Gelsolin); GSTP1; glycoprotein IIb; glycoprotein Illa; HAVCR2; HDAC4; HDAC5; HDAC7A; HDAC9; Her2; HGF; HIF1A; HIP1; histamine and histamine receptors; HLA-A; HLA-DRA; HM74; HMGB1; HMOX1; HUMCYT2A; ICEBERG; ICOSL; ID2; IFN-alpha; IFNA1; IFNA2; IFNA4; IFNA5; IFNA6; IFNA7; IFNB1; IFN-gamma; IFNW1; IGBP1; IGF1; IGF1R; IGF2; IGFBP2; IGFBP3; IGFBP6; IL-1; IL1A; IL1B; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; ILIA; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAKI; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); L-selectin; *LAMA5*; LEP (leptin); Lingo-p75; Lingo-Troy; LPS; LTA (TNF-b); LTB; LTB4R (GPR16); LTB4R2; LTBR; MAC-MARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSSI; MUCI (mucin); MYC; MYD88; NCK2; neurocan; NKG2D; NFKB1; NFKB2; NGF; NGFB (NGF); NGFR;

NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PARTI; PATE; PAWR; PCA3; PCNA; PDGFA; PDGFB; PECAM1; PF4 (CXCL4); PGE2; PGF; PGR; phosphacan; PIAS2; PIK3CG; plasmi-nogen activator; PLAU (uPA); PLG; PLXDC1; PPBP (CXCL7); PPID; PR1; PRKCQ; PRKDI; PRL; PROC; Protein C; PROK2; PSAP; PSCA; PTAFR; PTEN; PTGS2 (COX-2); PTN; RAC2 (p21Rac2); RAGE; RARB; RGSI; RGS13; RGS3; RNFIIO (ZNF144); ROB02; SI00A2; SCGB1D2 (lipophilin B); SCGB2A1 (mammaglobin 2); SCGB2A2 (mammaglobin 1); SCYE1 (endothelial Mono-cyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Sprl); ST6GAL1; STAB1; STAT6; STEAP; STEAP2; substance P; TB4R2; TBX21; TCP10; TDGF1; TEK; TGFA; TGFB1; TGFB111; TGFB2; TGFB3; TGFBI; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF-alpha; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSFIO (TRAIL); TNFSF11 (TRANCE); TNFSF12 (AP03L); TNFSF13 (April); TNFSF13B; TNFSF14 (HVEML); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TREM1; TREM2; TRPC6; TSLP; TWEAK; thrombomodulin; thrombin; VEGF; VEGFB; VEGFC; ver-sican; VHL C5; VLA-4; XCL1 (lymphotactin); XCL2 (SCM-lb); XCR1 (GPR5/CCXCR1); YY1; and ZFPM2.

16. The aAb of claim 12, wherein the first antigen binding site binds a T-cell marker, or wherein the T-cell marker is selected from CTLA-4, PD-1, Lag3, S15, B7H3, B7H4, TCR-alpha, TCR-beta, TIM-3, or wherein the first antigen binding site binds a T-cell activator, or wherein the T-cell activator is selected from CD3, 41BB or OX40.

17. The aAb of claim 14, wherein the second antigen binding site binds a T-cell marker, or wherein the T-cell marker is selected from CTLA-4, PD-1, Lag3, S15, B7H3, B7H4, TCR-alpha, TCR-beta, TIM-3, or wherein the second antigen binding site binds a T-cell activator, or wherein the T-cell activator is selected from CD3, 41BB or OX40.

18. The aAb of claim 12, wherein the cleavable linker is:

a protease cleavable linker; or the cleavable linker is cleaved by a tumor associated protease: MMP1, MMP2, MMP3, MMP7, MMP9, MMP10, MMP11, MMP12, MMP13, MMP14, MMP15, MMP16, MMP17, MMP19, MMP20, MMP21, uPA, FAPa, or Cathepsin B; or the cleavable linker is cleaved by proteases upregulated during apoptosis or inflammation associated responses; or the cleavable linker is cleaved by a caspase; and the caspase is Caspase 1, Caspase 2, Caspase 3, Caspase 4, Caspase 5, Caspase 6, Caspase 7, Caspase 8, Caspase 9, Caspase 10, Caspase 11 or Caspase 12.

19. The aAb of claim 12, wherein the cleavable linker does not mask an antigen binding site.

20. The aAb of claim 12, further comprising an agent conjugated to the aAb, or wherein the agent is at least one of: a toxin or toxic fragment thereof; a microtubule inhibitor; a nucleic acid damaging agent; a detectable moiety; or a diagnostic agent.

21. The aAb of claim 12, wherein the aAb comprises an amino acid sequence selected from SEQ ID NOS: 1, 2, or 3.

22. A nucleic acid that encodes an aAb, wherein the aAb encoded by the nucleic acid comprises, in order, the following structure:

a first light chain comprising:

a first variable light region and constant light region;

a first heavy chain consisting of:

a first variable heavy region, a constant heavy region, and an Fc region; and a cleavable linker between the constant light region and the first variable heavy region;

wherein the cleavable linker prevents or reduces the first variable heavy region from pairing with the first variable light region to form a first antigen binding site against a first antigen; and wherein cleavage of the cleavable linker releases the first variable heavy region to pair with the first variable light region to form the first antigen binding site to bind a first antigen.

23. A cell that comprises a nucleic acid that encodes an aAb of claim 22.

24. An activatable Antibody (aAb), in order, comprising:

a first variable light region;

a cleavable linker;

a first variable heavy region; and an Fc region;

wherein the cleavable linker prevents or reduces the first variable heavy region from pairing with the first variable light region to form a first antigen binding site against a first antigen, wherein the cleavable linker does not mask the antigen binding site; and wherein cleavage of the cleavable linker releases the first variable heavy region to pair with the first variable light region to form the first antigen binding site to bind a first antigen.

25. A cell that expresses an activatable antibody (aAb) comprising, in order, the following structure:

a first light chain comprising:

a first variable light region;

a cleavable linker; and a first heavy chain comprising:

a first variable heavy region;

wherein the cleavable linker prevents or reduces the first variable heavy region from pairing with the first variable light region to form a first antigen binding site against a first antigen; and wherein cleavage of the cleavable linker releases the first variable heavy region to pair with the first variable light region to form the first antigen binding site to bind a first antigen.

26. The cell of claim 25, wherein the cell is a T cell or a mesenchymal stem cell.

27. The cell of claim 25, wherein the aAb further comprises a transmembrane sequence that anchors the aAb to the surface of a T cell to form a chimeric antigen receptor, wherein the cell is a CAR T cell.

28. An activatable antibody (aAb) comprising, in order, the following structure: a first light chain comprising:

a first variable light region;

a cleavable linker; and a first heavy chain comprising:

a first variable heavy region;

wherein the cleavable linker prevents or reduces the first variable heavy region from pairing with the first variable light region to form a first antigen binding site against a first antigen;

wherein cleavage of the cleavable linker releases the first variable heavy region to pair with the first variable light region to form the first antigen binding site to bind a first antigen; and wherein the aAb does not contain a masking moiety that blocks an antigen binding site.

29. A nucleic acid that encodes an aAb, wherein the aAb encoded by the nucleic acid comprises, in order, the following structure:

a first light chain comprising:

a first variable light region;

a cleavable linker; and a first heavy chain comprising:

a first variable heavy region;

wherein the cleavable linker prevents or reduces the first variable heavy region from pairing with the first variable light region to form a first antigen binding site against a first antigen;

wherein cleavage of the cleavable linker releases the first variable heavy region to pair with the first variable light region to form the first antigen binding site to bind a first antigen; and wherein the aAb does not contain a masking moiety that blocks an antigen binding site.

30. A cell that comprises a nucleic acid that encodes an aAb of claim 29.

31. The aAb of claim 14, wherein the first and second antigen are at least one of:

the same antigen; the first and second antigen are different; or the first and second antigen is the same antigen but the first antigen binding site and the second antigen binding site bind different epitopes of the same antigen;

the first antigen binding site or the second antigen binding site binds a tumor target; or the tumor target is selected from a tumor targeting antigen, HER1, HER2, HER3, GD2, carcinoembryonic antigens (CEAs), epidermal growth factor receptor active mutant (EGFRVIII), CD133, fibroblast Activation Protein Alpha (FAP), epithelial cell adhesion molecular (Epcam), glypican 3 (GPC3), EPH Receptor A4 (EphA), tyrosine-protein kinase Met (cMET), IL-13Ra2, microsomal epoxide hydrolase (mEH), MAGE, Mesothelin, MUC16, MUC1, prostate stem cell antigen (PSCA), Wilms tumor-1 (WT-1), or a Claudin family member.

\* \* \* \* \*

SEQUENCE LISTING

```
<160> NUMBER OF SEQ ID NOS: 3

<210> SEQ ID NO 1
<211> LENGTH: 475
<212> TYPE: PRT
<213> ORGANISM: Artificial Sequence
<220> FEATURE:
<223> OTHER INFORMATION: Synthetic peptide

<400> SEQUENCE: 1

Met Ile Asn Glu Phe Ser Ser Leu Ala Gly Ala Gln Arg Gln Arg Leu
1               5                   10                  15

Leu Gly Val Val Val Val Gln Ser Leu Val His His Gly Ala Ala Lys
            20                  25                  30

His Val Ala Leu Leu Pro Ser Ala Leu Val His Cys Gln Ile Ala Ser
        35                  40                  45

Glu Ser Lys Ala Ala Val Gly Ile Gln His Gly His Gly Gly Leu Val
    50                  55                  60

Val Val Leu Gly Leu Ala Val Ala Phe Pro Phe His Gly Asp Ile Ala
65                  70                  75                  80

Arg Val Glu Ala Leu His Gln Thr Ala Gln Arg His Leu Ile Leu Gly
            85                  90                  95

Gln Leu Val Ser Ala Gly Arg Leu Gly Val His Leu Arg Leu Pro Arg
            100                 105                 110

Leu Ala Phe Gly Leu Ala Asp Gly Leu Leu Asn Gly Gly Gly Gln Ser
        115                 120                 125

Leu Val Gly Asp Leu Ala Leu Val Leu Leu Ala Val Glu Pro Val Leu
    130                 135                 140

Val Gln His Gly Gln His Gly His His Ser Ile Cys Gly Val Val Leu
145                 150                 155                 160

Leu Leu Ser Gly Leu Gly Phe Gly Val Val His Phe Asp Ala Val His
            165                 170                 175

Val Pro Val Lys Leu His Leu Gly Val Leu Met Ala Asp Val His His
            180                 185                 190

His Ala Cys His Leu Gly Cys Ser Arg Asp His Gln Cys Ile Leu Gly
        195                 200                 205

Phe Gly Arg Glu Gln Lys His Gly Arg Ser Ala Gln Gln Phe Gly Ser
    210                 215                 220

Arg Thr Ala Arg Asn Arg Tyr His Arg Ala Leu Thr Pro Ile Val Glu
225                 230                 235                 240

Val Ala Gly Leu Thr Arg Thr Val Ile Ser Arg Gly Val Leu Gly Gly
            245                 250                 255
```

-continued

```
Tyr Arg Val Asn Leu Gln Lys Glu Leu Val Phe Arg Gly Val Thr Gly
            260                 265                 270

Asp Arg Asp Thr Arg Phe Asp Arg Arg Val Val Ile Gly Arg Thr Phe
            275                 280                 285

Ile Ile Asp Glu Thr His Pro Phe Asn Phe Leu Thr Trp Glu Leu Thr
            290                 295                 300

Asp Pro Ile Pro Thr Ile Thr Gly Gly Asp Gly Gly Ala Gly Asn Arg
305                 310                 315                 320

Ala Arg Gln Ala Glu Arg Thr Gly Arg Ile Asn Gln Thr Arg Thr Arg
            325                 330                 335

Phe Phe Gln Phe Tyr Leu Ser Ala Tyr Val Leu Thr Pro Pro Phe Asp
            340                 345                 350

Phe Gln Leu Gly Ala Arg Thr Glu Arg Val Arg Ile Val Val Pro Leu
            355                 360                 365

Leu Ala Val Val Lys Arg Leu Val Phe Val Leu Asn Arg Arg Asn Gly
            370                 375                 380

Gln Arg Glu Val Gly Thr Arg Ala Arg Thr Thr Glu Thr Val Arg Asn
385                 390                 395                 400

Ala Gly Val Thr Gly Arg Arg Val Val Asp Gln Gln Phe Arg Arg Leu
            405                 410                 415

Thr Arg Leu Leu His Val Pro Ile Gln Ile Val Gly Phe Arg Val Arg
            420                 425                 430

Val Glu Gln Ala Leu Arg Ala Phe Ala Arg Asp Gly Arg Phe Phe Thr
            435                 440                 445

Arg Arg His Ala Gln Arg Arg Trp Arg Leu Gly His His Asn Val Ser
            450                 455                 460

Gly Gly Thr Trp Asn Pro Glu Gln Gln Tyr Pro
465                 470                 475

<210> SEQ ID NO 2
<211> LENGTH: 703
<212> TYPE: PRT
<213> ORGANISM: Artificial Sequence
<220> FEATURE:
<223> OTHER INFORMATION: Synthetic peptide

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Ser Cys Lys Ser Ser Gln Ser
            35                  40                  45

Leu Leu Asn Ser Gly Asn Gln Lys Asn Tyr Leu Thr Trp Tyr Gln Gln
            50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
            85                  90                  95

Phe Thr Leu Thr Ile Ser Ser Leu Gln Ala Glu Asp Val Ala Val Tyr
            100                 105                 110

Tyr Cys Gln Asn Asp Tyr Phe Tyr Pro Phe Thr Phe Gly Gln Gly Thr
            115                 120                 125

Lys Leu Glu Ile Lys Arg Thr Val Ala Ala Pro Ser Val Phe Ile Phe
            130                 135                 140
```

-continued

```
Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

Gly Ser Ser Gly Arg Ser Glu Asn Ile Arg Thr Ala Gly Gly Ser Gln
                245                 250                 255

Val Gln Leu Val Gln Ser Gly Ala Glu Val Lys Lys Pro Gly Ser Ser
            260                 265                 270

Val Lys Val Ser Cys Lys Ala Ser Gly Tyr Ala Phe Ser Asn Tyr Leu
        275                 280                 285

Ile Glu Trp Val Lys Gln Ala Pro Gly Gln Gly Leu Glu Trp Ile Gly
        290                 295                 300

Leu Ile Asn Pro Gly Ser Gly Gly Thr Asn Tyr Asn Glu Lys Phe Lys
305                 310                 315                 320

Gly Lys Ala Thr Ile Thr Ala Asp Lys Ser Thr Ser Thr Ala Tyr Met
                325                 330                 335

Glu Leu Ser Ser Leu Arg Ser Glu Asp Thr Ala Val Tyr Tyr Cys Ala
                340                 345                 350

Arg Val Tyr Tyr Gly Asn Ser Phe Ala Tyr Trp Gly Gln Gly Thr Leu
            355                 360                 365

Val Thr Val Ser Ser Ala Ser Thr Lys Gly Pro Ser Val Phe Pro Leu
        370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
            420                 425                 430

Ser Gly Leu Tyr Ser Leu Ser Ser Val Val Thr Val Pro Ser Ser Ser
        435                 440                 445

Leu Gly Thr Gln Thr Tyr Ile Cys Asn Val Asn His Lys Pro Ser Asn
        450                 455                 460

Thr Lys Val Asp Lys Arg Val Glu Pro Lys Ser Cys Asp Lys Thr His
465                 470                 475                 480

Thr Cys Pro Pro Cys Pro Ala Pro Glu Leu Leu Gly Gly Pro Ser Val
                485                 490                 495

Phe Leu Phe Pro Pro Lys Pro Lys Asp Thr Leu Met Ile Ser Arg Thr
                500                 505                 510

Pro Glu Val Thr Cys Val Val Val Asp Val Ser His Glu Asp Pro Glu
            515                 520                 525

Val Lys Phe Asn Trp Tyr Val Asp Gly Val Glu Val His Asn Ala Lys
        530                 535                 540

Thr Lys Pro Arg Glu Glu Gln Tyr Asn Ser Thr Tyr Arg Val Val Ser
545                 550                 555                 560
```

-continued

```
Val Leu Thr Val Leu His Gln Asp Trp Leu Asn Gly Lys Glu Tyr Lys
                565                 570                 575

Cys Lys Val Ser Asn Lys Ala Leu Pro Ala Pro Ile Glu Lys Thr Ile
                580                 585                 590

Ser Lys Ala Lys Gly Gln Pro Arg Glu Pro Gln Val Tyr Thr Leu Pro
                595                 600                 605

Pro Ser Arg Asp Glu Leu Thr Lys Asn Gln Val Ser Leu Thr Cys Leu
            610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Tyr Ser Lys Leu Thr Val Asp Lys Ser Arg
                660                 665                 670

Trp Gln Gln Gly Asn Val Phe Ser Cys Ser Val Met His Glu Ala Leu
                675                 680                 685

His Asn His Tyr Thr Gln Lys Ser Leu Ser Leu Ser Pro Gly Lys
            690                 695                 700

<210> SEQ ID NO 3
<211> LENGTH: 963
<212> TYPE: PRT
<213> ORGANISM: Artificial Sequence
<220> FEATURE:
<223> OTHER INFORMATION: Synthetic peptide

<400> SEQUENCE: 3

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Asp Ser Leu Ala
                20                  25                  30

Val Ser Leu Gly Glu Arg Ala Thr Ile Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
                100                 105                 110

Tyr Cys Gln Asn Asp Tyr Phe Tyr Pro Phe Thr Phe Gly Gln Gly Thr
            115                 120                 125

Lys Leu Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220
```

-continued

```
Gln Gly Leu Ser Ser Pro Val Thr Lys Ser Phe Asn Arg Gly Glu Cys
225             230                 235                 240

Gly Ser Ser Gly Arg Ser Glu Asn Ile Arg Thr Ala Gly Gly Ser Gln
                245                 250                 255

Val Gln Leu Val Gln Ser Gly Ala Glu Val Lys Lys Pro Gly Ser Ser
                260                 265                 270

Val Lys Val Ser Cys Lys Ala Ser Gly Tyr Ala Phe Ser Asn Tyr Leu
            275                 280                 285

Ile Glu Trp Val Lys Gln Ala Pro Gly Gln Gly Leu Glu Trp Ile Gly
        290                 295                 300

Leu Ile Asn Pro Gly Ser Gly Gly Thr Asn Tyr Asn Glu Lys Phe Lys
305                 310                 315                 320

Gly Lys Ala Thr Ile Thr Ala Asp Lys Ser Thr Ser Thr Ala Tyr Met
                325                 330                 335

Glu Leu Ser Ser Leu Arg Ser Glu Asp Thr Ala Val Tyr Tyr Cys Ala
                340                 345                 350

Arg Val Tyr Tyr Gly Asn Ser Phe Ala Tyr Trp Gly Gln Gly Thr Leu
            355                 360                 365

Val Thr Val Ser Ser Ala Ser Thr Lys Gly Pro Ser Val Phe Pro Leu
        370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
                420                 425                 430

Ser Gly Leu Tyr Ser Leu Ser Ser Val Val Thr Val Pro Ser Ser Ser
            435                 440                 445

Leu Gly Thr Gln Thr Tyr Ile Cys Asn Val Asn His Lys Pro Ser Asn
        450                 455                 460

Thr Lys Val Asp Lys Arg Val Glu Pro Lys Ser Cys Asp Lys Thr His
465                 470                 475                 480

Thr Cys Pro Pro Cys Pro Ala Pro Glu Ala Ala Gly Gly Pro Ser Val
                485                 490                 495

Phe Leu Phe Pro Pro Lys Pro Lys Asp Thr Leu Met Ile Ser Arg Thr
                500                 505                 510

Pro Glu Val Thr Cys Val Val Val Asp Val Ser His Glu Asp Pro Glu
            515                 520                 525

Val Lys Phe Asn Trp Tyr Val Asp Gly Val Glu Val His Asn Ala Lys
        530                 535                 540

Thr Lys Pro Arg Glu Glu Gln Tyr Asn Ser Thr Tyr Arg Val Val Ser
545                 550                 555                 560

Val Leu Thr Val Leu His Gln Asp Trp Leu Asn Gly Lys Glu Tyr Lys
                565                 570                 575

Cys Lys Val Ser Asn Lys Ala Leu Gly Ala Pro Ile Glu Lys Thr Ile
            580                 585                 590

Ser Lys Ala Lys Gly Gln Pro Arg Glu Pro Gln Val Tyr Thr Leu Pro
            595                 600                 605

Pro Ser Arg Asp Glu Leu Thr Lys Asn Gln Val Ser Leu Thr Cys Leu
        610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
```

-continued

```
                       645                    650                    655

Asp Gly Ser Phe Phe Leu Tyr Ser Lys Leu Thr Val Asp Lys Ser Arg
                660                    665                    670

Trp Gln Gln Gly Asn Val Phe Ser Cys Ser Val Met His Glu Ala Leu
            675                    680                    685

His Asn His Tyr Thr Gln Lys Ser Leu Ser Leu Ser Pro Gly Lys Gly
        690                    695                    700

Gly Gly Gly Ser Gly Gly Gly Gly Ser Gly Gly Gly Ser Gly Gly
705                    710                    715                    720

Gly Gly Ser Gln Ile Val Leu Thr Gln Ser Pro Ala Ile Met Ser Ala
                725                    730                    735

Ser Pro Gly Glu Lys Val Thr Met Thr Cys Ser Ala Ser Ser Ser Val
                740                    745                    750

Ser Tyr Met Asn Trp Tyr Gln Gln Lys Ser Gly Thr Ser Pro Lys Arg
            755                    760                    765

Trp Ile Tyr Asp Thr Ser Lys Leu Ala Ser Gly Val Pro Ala His Phe
    770                    775                    780

Arg Gly Ser Gly Ser Gly Thr Ser Tyr Ser Leu Thr Ile Ser Gly Met
785                    790                    795                    800

Glu Ala Glu Asp Ala Ala Thr Tyr Tyr Cys Gln Gln Trp Ser Ser Asn
                805                    810                    815

Pro Phe Thr Phe Gly Ser Gly Thr Lys Leu Glu Ile Asn Gly Gly Gly
                820                    825                    830

Gly Ser Gly Gly Gly Gly Ser Gly Gly Gly Gly Ser Gln Val Gln Leu
            835                    840                    845

Gln Gln Ser Gly Ala Glu Leu Ala Arg Pro Gly Ala Ser Val Lys Met
    850                    855                    860

Ser Cys Lys Ala Ser Gly Tyr Thr Phe Thr Arg Tyr Thr Met His Trp
865                    870                    875                    880

Val Lys Gln Arg Pro Gly Gln Gly Leu Glu Trp Ile Gly Tyr Ile Asn
                885                    890                    895

Pro Ser Arg Gly Tyr Thr Asn Tyr Asn Gln Lys Phe Lys Asp Lys Ala
            900                    905                    910

Thr Leu Thr Thr Asp Lys Ser Ser Ser Thr Ala Tyr Met Gln Leu Ser
        915                    920                    925

Ser Leu Thr Ser Glu Asp Ser Ala Val Tyr Tyr Cys Ala Arg Tyr Tyr
    930                    935                    940

Asp Asp His Tyr Cys Leu Asp Tyr Trp Gly Gln Gly Thr Thr Leu Thr
945                    950                    955                    960

Val Ser Ser
```